United States Patent
Dubewar et al.

(10) Patent No.: US 11,872,305 B2
(45) Date of Patent: Jan. 16, 2024

(54) STABLE PHARMACEUTICAL COMPOSITIONS OF SUCCINYLCHOLINE CHLORIDE

(71) Applicant: Slayback Pharma LLC, Princeton, NJ (US)

(72) Inventors: Ashish Anilrao Dubewar, Hyderabad (IN); Amit Anil Charkha, Wardha (IN); Sumitra Ashokkumar Pillai, Hyderabad (IN); Pradeep Kumar Kare, Hyderabad (IN); Kumar Swamy Ummiti, Hyderabad (IN); Shanker Mamidi, Nalgonda (IN); Mayur Anshiram Adhav, Hyderabad (IN)

( * ) Notice: Subject to any disclaimer, the term of this patent is extended or adjusted under 35 U.S.C. 154(b) by 0 days.

(21) Appl. No.: 17/822,756

(22) Filed: Aug. 26, 2022

(65) Prior Publication Data

US 2023/0091021 A1   Mar. 23, 2023

(30) Foreign Application Priority Data

Aug. 27, 2021 (IN) .............................. 202141038846

(51) Int. Cl.
| | |
|---|---|
| *A01N 37/00* | (2006.01) |
| *A61K 31/215* | (2006.01) |
| *A01N 37/12* | (2006.01) |
| *A01N 37/44* | (2006.01) |
| *A61K 31/24* | (2006.01) |
| *A01N 25/00* | (2006.01) |
| *A61K 9/00* | (2006.01) |
| *A61K 47/18* | (2017.01) |
| *A61K 47/10* | (2017.01) |
| *A61K 31/225* | (2006.01) |
| *A61K 31/221* | (2006.01) |
| *A61K 47/12* | (2006.01) |

(52) U.S. Cl.
CPC .......... *A61K 9/0019* (2013.01); *A61K 31/221* (2013.01); *A61K 31/225* (2013.01); *A61K 47/10* (2013.01); *A61K 47/12* (2013.01); *A61K 47/183* (2013.01)

(58) Field of Classification Search
None
See application file for complete search history.

(56) References Cited

U.S. PATENT DOCUMENTS 5,962,536 A * 10/1999 Komer ................. A61K 31/225
                                                        514/731

FOREIGN PATENT DOCUMENTS

FR             2716 M   *   8/1964   ............. A61K 31/16

* cited by examiner

*Primary Examiner* — Layla Soroush
(74) *Attorney, Agent, or Firm* — Sarika Singh

(57) ABSTRACT

The present invention relates to injectable pharmaceutical compositions comprising therapeutically effective amount of succinylcholine chloride, one or more pharmaceutically acceptable aqueous solvents, and one or more stabilizing agents selected from aliphatic polyols; lower alkyl alcohols; amino acids having at least one additional amino, carboxyl or hydroxyl group; amino alcohols; and aliphatic dicarboxylic acids having at least one hydroxyl or amino group, or α-β unsaturation. The compositions are stable at room temperature for at least 30 days. Methods of manufacturing the injectable pharmaceutical compositions are also provided. The composition may be provided in a sealed container, e.g., an ampoule, vial and pre-filled syringe, and are suitable for subcutaneous, intravenous or intramuscular administration as an adjunct to general anesthesia, to facilitate tracheal intubation, and/or to provide skeletal muscle relaxation during surgery or mechanical ventilation.

13 Claims, No Drawings

STABLE PHARMACEUTICAL COMPOSITIONS OF SUCCINYLCHOLINE CHLORIDE

CROSS-REFERENCE TO RELATED APPLICATIONS

This application claims the benefit of Indian Patent Application No. 202141038846 filed Aug. 27, 2021, which is incorporated by reference herein in its entirety.

FIELD OF THE INVENTION

The present invention relates to stable injectable pharmaceutical compositions of succinylcholine chloride or pharmaceutically acceptable solvates, or hydrates thereof and methods for manufacturing the same. The composition may be provided in a sealed container, e.g., an ampoule, vial and pre-filled syringe, and are suitable for subcutaneous, intravenous or intramuscular administration.

BACKGROUND OF THE INVENTION

Succinylcholine chloride is a di-quaternary base consisting of the dichloride salt of the dicholine ester of succinic acid. Succinylcholine is a short-acting, depolarizing-type, skeletal muscle relaxant. Succinylcholine has long been the favoured neuromuscular blocking agent and drug of choice for emergent airway management because of its rapid onset, dependable effect, and short duration. Succinylcholine combines with the cholinergic receptors of the motor end plate to produce depolarization. This depolarization may be observed as fasciculations. Subsequent neuromuscular transmission is inhibited so long as adequate concentration of succinylcholine remains at the receptor site. Onset of flaccid paralysis is rapid (less than one minute after intravenous administration), and single administration lasts approximately 4 to 6 minutes. The chemical name of succinylcholine chloride is 2,2'-[(1,4-dioxo-1,4-butanediyl)bis(oxy)]bis[N,N,Ntrimethylethanaminium] dichloride and its chemical structure is represented by the structural Formula (I).

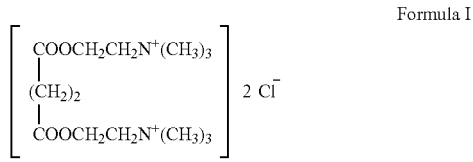

Formula I

Succinylcholine chloride is freely soluble in water, slightly soluble in alcohol and practically insoluble in ether. Succinylcholine chloride has been approved as an adjunct to general anaesthesia, to facilitate tracheal intubation, and to provide skeletal muscle relaxation during surgery or mechanical ventilation.

Succinylcholine chloride is currently approved and marketed in the United States under the brand names ANECTIN® and QUELICIN®. For short surgical procedures in adults, recommended optimum dose varies among individuals and may be from 0.3 to 1.1 mg/kg succinylcholine injection given intravenously to produce neuromuscular blockade and to facilitate tracheal intubation. For long surgical procedures, the dose of succinylcholine administered by infusion, after diluting to concentration from 1 mg/mL to 2 mg/mL, depends upon the duration of the surgical procedure and the need for muscle relaxation. The average rate of infusion for an adult range between 2.5 and 4.3 mg per minute.

Succinylcholine chloride may be present in ionized form in aqueous solution practically all over the ranges of pH because of the presence of a quaternary ammonium salt. Since the hydrolytic cleavage of ordinary esters is catalysed by hydrogen and/or hydroxyl ions, it is considered that the ester-linkages in succinylcholine chloride might also be subject to hydrogen or hydroxyl ion catalysing reaction.

The hydrolysis of succinylcholine is catalyzed by both hydrogen ions and hydroxyl ions. Succinylcholine in aqueous solution hydrolyzes rapidly to form an inactive monoester (succinylmonocholine), which subsequently undergoes much slower hydrolysis to yield choline and succinic acid. During the degradation of succinylcholine, production of succinic acid decreases the pH value and speeds up the hydrolysis reaction. Finally, the rate of hydrolysis remains constant because of the slow down effect of the decreased succinylcholine concentration (Adnet et al., Emerg Med J 2007; 24:168-169).

Succinylcholine solutions are often kept at room temperature in emergency resuscitation carts, because of the need for immediate availability in emergency room settings. This presents a challenge because succinylcholine decomposes at a considerably higher rate when the temperature is elevated. Injectable formulations containing succinylcholine chloride are very challenging to manufacture since they degrade rapidly at elevated temperatures. In order to compensate for the loss of succinylcholine at elevated temperatures, it is a common practice to add overages while manufacturing the composition.

All commercially available injections of succinylcholine chloride are stored at 2° C. to 8° C. Commercial Succinylcholine chloride injections in the original unopened containers are stable for 14 days at room temperature.

International publication no. WO2022018177A1 ("Aguettant") seeks to ameliorate a need to dilute commercial solutions of succinylcholine chloride (having concentrations of 20-50 mg/ml), which is associated with risks of medical errors, contamination concerns and reduced shelf life of diluted solutions. Aguettant is said to provide ready to use aqueous solution of succinylcholine chloride having a concentration of 10 mg/ml buffered at a pH ranging from 3.0 to 4.5 with succinic acid, at a concentration ranging from 5 mM to 20 mM, having stability at 2-8° C. of up to 24 months and at room temperature for up to 3 months. Aguettant asserts that the selection of the specified concentration of succinic acid in the composition was essential for avoiding pH modification during the shelf life and ensure stability as it provides sufficient buffering without increase in degradation kinetics of succinylcholine, triggered by lower pH inherent with high concentrations of succinic acid. The publication also provides a preferred process of steam sterilization at 121° C. of the composition wherein succinylcholine chloride overages of 5% are used to compensate for degradation during the manufacturing and storage of the composition. However, the only example of the claimed composition that show stability of the composition at room temperature for several months combine the specified succinic acid concentration, pH range, and steam sterilization.

When succinylcholine injection is placed along with other potent drugs used in emergency room settings, accidental mix-up and administration of unintended drug may occur. There is an imminent risk of death due to medication errors. Accidental administration of succinylcholine may lead to respiratory arrest and death. It is very important to confirm proper selection of intended drug and avoid confusion with other injectable solutions that are present in critical care and other clinical settings.

The factors described above influence the safety, quality & efficacy of finished product comprising succinylcholine. Because of the problems associated with manufacture, storage and manner of use of succinylcholine described above and the limitations with currently available products of succinylcholine chloride, it is desirable to develop a stable injectable succinylcholine chloride solution for human use, which is safe, therapeutically effective, easy to differentiate from look-a-like injections, ready to dilute or ready to administer, and has prolonged room temperature stability without any significant loss of potency.

The present invention fulfils this need by developing stable injectable solutions of succinylcholine chloride and providing methods of efficient and safer use to achieve an improved standard of patient care.

SUMMARY OF THE INVENTION

The present invention relates to stable injectable solutions of succinylcholine chloride, suitable for human use, with prolonged room temperature stability compared to the currently approved and marketed dosage forms of succinylcholine chloride and without any significant loss of potency.

The injectable pharmaceutical composition of the present invention comprises:
  (i) therapeutically effective amount of succinylcholine chloride;
  (ii) one or more stabilizing agents;
  (iii) one or more pharmaceutically acceptable solvents,
  wherein the composition is stable at room temperature for at least 30 days,
  wherein water is at least one of the pharmaceutically acceptable solvents, and
  wherein the stabilizing agents are selected from the group consisting of aliphatic polyols; lower alkyl alcohols; amino acids having at least one additional amino, carboxyl or hydroxyl group; amino alcohols; and aliphatic dicarboxylic acids having at least one hydroxyl or amino group, or α-β unsaturation.

In one aspect of the invention, the injectable pharmaceutical composition is free of tonicity contributing agent.

In another aspect, the injectable pharmaceutical composition has total impurities of less than about 6.0% (w/w) as measured by HPLC, when stored at 25° C./40% RH for up to 90 days.

In yet another aspect, the i injectable pharmaceutical composition has succinic acid impurity of less than about 0.5% (w/w) as measured by HPLC, when stored at 25° C./40% RH for up to 90 days.

In yet other aspects, the injectable pharmaceutical composition has succinylmonocholine impurity of less than about 5.0% (w/w) as measured by HPLC, when stored at 25° C./40% RH for up to 90 days.

In other aspects, the injectable pharmaceutical composition has choline impurity of less than about 3.0% (w/w) as measured by HPLC, when stored at 25° C./40% RH for up to 90 days.

The inventive injectable pharmaceutical composition may be sterilized using a technique selected from the group consisting of filtration through aseptic filtration-filling-sealing process, terminal sterilization, incorporation of sterilizing agents, irradiation, and heating.

In another aspect, the injectable pharmaceutical composition is disposed in a pre-filled syringe or vial.

In yet another aspect, the invention provides a kit comprising an injection device for administration of the injectable pharmaceutical composition to a subject in need of such pharmaceutical composition, wherein the injection device comprises a needle and prefilled syringe or syringe cartridge with the composition disposed therein.

In another aspect, the injectable pharmaceutical composition further comprises one or more pharmaceutically acceptable excipients selected from the group consisting of buffering agents, pH adjusting agents, tonicity contributing agents, antioxidants, chelating agents and preservatives.

In a further aspect, the injectable pharmaceutical composition upon intravenous or intramuscular administration exhibits bioequivalence to a commercially available reference succinylcholine chloride drug products (such as ANECTIN® and QUELICIN®), and wherein said bioequivalence is established by at least one of: (i) a confidence interval for mean AUC0-t between about 80% and about 125%; (ii) a confidence interval for mean AUC0-infinity between about 80% and about 125%; (iii) a confidence interval for mean Cmax between about 80% and about 125% or a combination thereof.

In certain aspects, the invention relates to methods for making the injectable pharmaceutical composition, which comprise: (i) dispensing 80% v/v water for injection; (ii) sequentially adding stabilizing agent and stirring to form solution-1; (iii) adding succinylcholine chloride to solution-1 and stirring to form solution-2; (iv) adjusting the pH of the solution-2 by adding a suitable pH adjusting agent; (v) making up the final volume with remaining water for injection to obtain final solution; (vi) purging nitrogen gas throughout the procedure; (vii) filtering the final solution; (viii) filling the solution in pre-filled syringes or vials and stoppering with coated stoppers.

In another aspect, the present invention relates to methods of treatment comprising administration of the injectable pharmaceutical compositions of the invention to a subject in need thereof, as an adjunct to general anesthesia, to facilitate tracheal intubation, and/or to provide skeletal muscle relaxation during surgery or mechanical ventilation.

The inventive pharmaceutical compositions are suitable for parenteral administration via subcutaneous, intravenous or intramuscular routes and are provided in the form of aqueous solution.

The inventive injectable pharmaceutical compositions are advantageously ready-to-use (RTU) or ready-to-dilute (RTD). An aspect of the invention relates to stable ready-to-use or ready-to-dilute succinylcholine chloride compositions suitable for parenteral administration.

In some embodiments, the succinylcholine chloride is present in the injectable pharmaceutical composition at a concentration of about 5 mg/mL to about 60 mg/mL, such as about 20 mg/mL.

In some embodiments, the injectable pharmaceutical composition has osmolality value of between about 100 mOsm and about 2000 mOsm.

In other embodiments, the injectable pharmaceutical composition has a pH in the range of from about 3 to about 5.

In some embodiments, the stabilizing agent is selected from the group consisting of propylene glycol, polyethylene glycol, glycerol, cyclodextrin, cyclodextrin derivatives, ethanol, glutamic acid, aspartic acid, arginine, lysine, meglumine, diethanolamine, tromethamine, maleic acid, tartaric acid, and mixtures thereof.

In some embodiments, the injectable pharmaceutical composition comprises aliphatic polyols and/or lower alkyl alcohols as stabilizers at a concentration of less than about 300 mg/mL.

In some embodiments, the injectable pharmaceutical composition comprises stabilizers selected from the group consisting of amino acids having at least one additional amino, carboxyl or hydroxyl group; amino alcohols; aliphatic dicarboxylic acids having at least one hydroxyl or amino group, or $\alpha$-$\beta$ unsaturation; and mixtures thereof at a concentration of less than about 2 mg/mL.

In some embodiments, the pre-filled syringe is made up of a polymeric materials selected from the group consisting of polysulfone, polycarbonate, polypropylene, polyethylene, ethylene/propylene copolymers, polyolefins, acrylic-imide copolymers, polyester, poly (1,1,2,2 tetrafluoroethylene), Nylon, polyoxymethylene, polymethylpentene, polyvinylidene chloride, ethylvinylacetate, cyclic olefin polymer, cyclic olefin copolymer, crystal zenith, and mixtures thereof.

In one embodiment, the inventive injectable pharmaceutical composition comprises succinylcholine chloride at a concentration of about 20 mg/mL, propylene glycol, purified water, wherein the composition is free of sodium chloride, wherein the composition is disposed in a pre-filled syringe and is stable at room temperature for at least 30 days.

DETAILED DESCRIPTION OF THE INVENTION

Unless defined otherwise, all the technical and scientific terms used herein have the same meanings as commonly known by a person skilled in the art. In case there are a plurality of definitions for the terms herein, the definitions provided herein will prevail.

As used herein, the term "room temperature" means a temperature of from 59° F. to 77° F. (15° to 25° C.) that is suitable for human occupancy and at which laboratory experiments are usually performed.

As used herein, "a," "an," "the," "at least one," and "one or more" are used interchangeably. As used herein, the term "or" is generally employed in its usual sense including "and/or" unless the content clearly dictates otherwise.

As used herein the term "succinylcholine" refers to succinylcholine free base or a pharmaceutically acceptable salt, solvate or hydrate thereof.

As used herein, the term "about" means having a value falling within an accepted standard of error of the mean when considered by one of ordinary skill in the art. Frequently, the term "about" refers to ±20%, preferably ±10%, and more preferably ±5% of the value or range to which it refers.

Within the context of the present invention, the term "ready-to-use" or "RTU" as used herein refers to an injectable composition that is stable and is not reconstituted from a lyophilizate. The term "ready-to-use" or "RTU" also encompasses within its scope, injectable compositions that are stable and do not require any reconstitution or dilution with parenterally acceptable diluent and can be directly administered to the patient.

Within the context of the present invention, the term "ready-to-dilute" or "RTD" as used herein refers to an injectable composition that is stable and is diluted with a suitable diluent for parenteral administration.

The terms "composition", "pharmaceutical composition", "pharmaceutical product", "dosage form", "pharmaceutical dosage form", "formulation", "pharmaceutical formulation", etc., refer to a pharmaceutical composition that may be administered to a patient in need of treatment, which may be in any conventional formulation. For example, the term "pharmaceutical composition" as used herein refers to a solution for parenteral administration.

Within the context of this invention, the term "solution" refers to a mixture of one or more substances dispersed molecularly (i.e., dissolved) in a dissolving liquid medium or vehicle. The solution is preferably homogeneous, in the sense that the active pharmaceutical ingredient (API) is essentially uniformly distributed and concentrated in the solution. The liquid solution may be viscous or not. A solution differs from a suspension which comprises solid particles dispersed throughout a liquid phase in which they are not soluble. As used herein, the term "solution" further means a solution which does not contain any visible particulate matter, solid particle, liposome or nanoparticles. The solution provides % transmittance, when measured at 650 nm, of not less than 90%, not less than 95%, not less than 98%, not less than 99%, not less than 99.5%, not less than 99.7% or not less than 99.8%.

The terms "parenterally acceptable liquid vehicle", "vehicle", "solvent", "pharmaceutically acceptable solvent" and "parenterally acceptable liquid solvent" are interchangeable.

The term "pharmaceutically acceptable excipient" as used herein means a diluent, carrier, or composition auxiliary, which is non-toxic and inert, which does not have undesirable effects on a subject to whom it is administered and is suitable for delivering a therapeutically active agent to the target site without affecting the therapeutic activity of the active agent.

The terms "degradation product" or "impurity," as used herein, refer to unwanted chemical products (including, but not limited to known or unknown related substances) that can develop during the manufacturing, transportation, and/or storage of drug products and can affect the efficacy of pharmaceutical products. These products can form in response to changes in light, temperature, pH, and humidity, or due to inherent characteristics of active ingredient, such as their reaction with excipients or on contact with the packaging.

The term "parenteral" or "injectable" refers to routes selected from subcutaneous (SC), intravenous (IV), intramuscular (IM), intradermal (ID), intraperitoneal (IP) and the like.

The expression "bioequivalent" or "bioequivalence" is a term of art and is intended to be defined in accordance with Approved Drug Products with Therapeutic Equivalence Evaluations, 41$^{th}$ Edition, which is published by the U.S. Department of Health and Human Services, and is commonly known as the "Orange Book". Generally, bioequivalence can be defined as the absence of significant difference in the rate and extent to which the active ingredient or active moiety in pharmaceutical equivalents or pharmaceutical alternatives becomes available at the site of drug action when administered at the same molar dose under similar conditions in an appropriately designed study. Bioequivalence of different formulations of the same drug substance involves equivalence with respect to the rate and extent of drug absorption. The pharmacokinetic characteristics of the concentration-time curve, such as the maximum observed plasma concentration ($C_{max}$), the time to reach $C_{max}$, and the area under the plasma concentration versus time curve (AUC), are examined by statistical procedures which are well-established in the field of pharmacokinetics. Two formulations whose rate and extent of absorption differ by −20%425% or less are generally considered to be bioequivalent.

The term "in vivo" in general means in the living body of a plant or animal, whereas the term "in vitro" generally means outside the body and in an artificial environment.

The term "subject" refers to an animal, including a human or non-human. The terms patient and subject may be used interchangeably herein. Non-human may be a rat, a dog, a mouse or a guinea pig.

The term "peak time of plasma drug concentration ($T_{max}$)" means the time when peak plasma drug concentration ($C_{max}$) is attained after drug administration.

The term "peak plasma drug concentration (Cmax)" means the maximum plasma drug concentration attained after drug administration.

The term "$AUC_{0-infinity}$" means the area under a plasma drug concentration time curve from time point of 0 to infinity after drug administration.

The term "AUC0-t" means the area under a plasma drug concentration-time curve from time point of 0 to t after drug administration, wherein t is time in hours and is in between 1 hour to 72 hours.

As used herein, the term "storage" refers to the holding of a composition under controlled or uncontrolled conditions for a period ranging from a few minutes to several months or longer. Storage conditions that can be controlled include, for example, temperature, humidity, and the level of light. In many cases, storage of a pharmaceutical formulation is under industry acceptable standards and/or standards that are mandated by regulatory agencies, such as USFDA.

By "therapeutically effective" amount is meant the amount of a drug sufficient to treat, prevent, or ameliorate a condition in a subject or patient. The effective amount of succinylcholine chloride, used to practice the present invention for therapeutic management of a condition may be determined and adjusted by a person of ordinary skill to provide the appropriate amount and dosage regimen, e.g., depending upon one or more of the manners of administration, the age, body weight, sex, and/or general health of the patient.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

As used herein, "prolonged duration" refers to the holding of a composition under controlled or uncontrolled conditions for a period of more than 21 days.

As used herein, "significant loss of potency" means that no more than about a 10% loss of succinylcholine chloride occurs under typical commercial storage conditions.

The objective of the present invention is to increase the stability of succinylcholine chloride solution enabling stable injectable solution dosage forms which can remain stable at room temperature for prolonged duration. Another objective of the present invention is to provide injectable solutions of succinylcholine chloride which remain stable when stored at room temperature for prolonged duration without significant loss of potency. Yet another objective of the present invention is to provide stable injectable solutions of succinylcholine chloride which can be easily distinguishable from look-a-like injections when placed in emergency resuscitation carts and having stability for prolonged duration without significant loss of potency, when stored at room temperature.

The inventive pharmaceutical compositions described herein are provided in the form of a solution suitable for injection. To prepare such composition, active drug is dissolved in a parenterally acceptable liquid vehicle. The pharmaceutically acceptable liquid vehicle or solvent may comprise water, water for injection, saline, dextrose solution, dimethylacetamide, N-methyl-pyrrolidone, dimethyl sulfoxide, ringer's solution, isotonic sodium chloride solution, or suitable mixtures thereof.

According to the present invention, the compositions may be provided in a kit form along with a parenterally acceptable diluent. Parenterally acceptable diluents include water for injection, 0.9% saline (normal saline), 0.45% saline (half normal saline) and 2.5% dextrose/0.45% saline, ringer's lactate solution or mixtures thereof.

The present invention relates to injectable solution of succinylcholine chloride, particularly wherein succinylcholine chloride may be present at a concentration of 5 mg/mL or more. In another embodiment, stable injectable pharmaceutical compositions of the present invention comprise succinylcholine chloride, wherein succinylcholine chloride is present at concentration about 5 mg/mL to about 60 mg/mL, such as about 20 mg/mL.

Preferably, the stable pharmaceutical compositions for human use will be provided as a solution dosage form that is suitable for intravenous administration. The pharmaceutical compositions may be formulated according to conventional pharmaceutical practice. The compositions of the invention can be administered in any conventional manner. It will be readily appreciated by those skilled in the art how to administer compositions of the present invention to a human.

Stabilizing agents increase the stability of succinylcholine chloride in pharmaceutically acceptable vehicles. Succinylcholine chloride is hydrolytic in nature. Stabilizing agents markedly increase the stability of succinylcholine chloride in aqueous solutions. Stabilizing agents are selected from the group consisting of aliphatic polyols; lower alkyl alcohols; amino acids having at least one additional amino, carboxyl or hydroxyl group; amino alcohols; aliphatic dicarboxylic acids having at least one hydroxyl or amino group, or α-β unsaturation; and mixtures thereof.

Aliphatic polyols include aliphatic acyclic or cyclic compound having two or more hydroxy groups, such as glycerols, glycols and polymers thereof, and cyclic oligosaccharides. Examples of such polyols include propylene glycol, polyethylene glycol (e.g. polyethylene glycol 300, polyethylene glycol 400, polyethylene glycol 600), cyclodextrin, cyclodextrin derivatives, and mixtures thereof.

Lower alkyl alcohols include, ethanol, propanol, isopropanol, butanol, and the like.

Amino acids having at least one additional amino, carboxyl or hydroxyl group include glutamic acid, aspartic acid, arginine, lysine, and mixtures thereof.

Amino alcohols include meglumine, diethanolamine, tromethamine, and mixtures thereof Aliphatic dicarboxylic acids having at least one hydroxyl or amino group, or α-β unsaturation maleic acid, tartaric acid, and the like.

Cyclodextrins include α-cyclodextrin, β-cyclodextrin, δ-cyclodextrin, γ-cyclodextrin, or combinations thereof. In an embodiment, the cyclodextrin includes either a substituted or non-substituted β-cyclodextrin, particularly hydroxypropyl-β-cyclodextrin (HP-β-CD) and/or sulfobutylether-β-cyclodextrin (SBE-β-CD). However, it is understood that typically any substitution to the cyclodextrin, including substitution by hydrophobic groups such as hydroxyalkyl substituted-cyclodextrin, will improve its aqueous solubility by disrupting the hydrogen bonding network within the crystal lattice of the solid cyclodextrin, thereby lowering the lattice energy of the solid. The degree of substitution is not believed to be critical; however, the degree of substitution is advantageously at least 1% and typically 2% to 10%, such as 3% to 6%.

In an embodiment, the present invention provides stable injectable pharmaceutical composition comprising (a) therapeutically effective amount of succinylcholine chloride; (b) one or more pharmaceutically acceptable solvents; (c) one or more stabilizing agents selected from maleic acid, tartaric acid, glutamic acid, aspartic acid, propylene glycol, polyethylene glycol, ethanol, glycerine, arginine, lysine, meglumine, cyclodextrin derivatives, diethanolamine, tromethamine, and mixtures thereof; and (d) optionally, one or more other pharmaceutically acceptable excipients, wherein the concentration of stabilizing agent in the composition is less than about 300 mg/mL.

In an embodiment, the stable injectable pharmaceutical composition of the invention comprises (a) therapeutically effective amount of succinylcholine chloride; (b) one or more pharmaceutical acceptable solvents; (c) one or more stabilizing agents and (d) optionally, one or more additional pharmaceutically acceptable excipients, wherein the composition has a pH in the range of about 3.0 to about 5.0, such as in the range from about 3.0 to 4.5.

In another embodiment, the stable injectable pharmaceutical composition of the invention comprises (a) therapeutically effective amount of succinylcholine chloride; (b) one or more pharmaceutical acceptable solvents; (c) one or more stabilizing agents and (d) optionally, one or more additional pharmaceutically acceptable excipients, wherein the composition has osmolality value of between about 100 mOsm and about 4000 mOsm.

In an embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the composition is stable when stored at room temperature conditions for prolonged duration without significant loss of potency.

The pharmaceutically acceptable excipient(s) may be selected from, but are not limited to, co-solvents, surfactants, wetting agents, water immiscible solvents, water, water miscible solvents, hydrophilic solvents, hydrophobic solvents, preservatives, chelating agents, antioxidants, tonicity contributing agents, anti-foaming agents, buffering agents, pH adjusting agents, osmotic agents and the like or mixtures thereof.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the composition is stable for at least 15 days, for at least 30 days, for at least 60 days, or for at least 90 days when stored at 25° C./60% RH or 25° C./40% RH.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the composition is stable for at least 3 months, for at least 6 months, for at least 9 months, for at least 12 months, for at least 18 months, for at least 24 months, for at least 30 months, or for at least 36 months, when stored at 2° C. to 8° C.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the composition is stable for up to 90 days when stored at 25° C.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein said composition is stable at 2-8° C. for at least 18 months followed by storage at 25° C. for at least 30 days.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the level of each impurity in the composition is less than about 8% w/w, preferably less than about 6% w/w, more preferably less than about 5% w/w, more preferably less than about 2% w/w, more preferably less than about 1% w/w, more preferably less than about 0.1% w/w, more preferably less than about 0.1% w/w as measured by HPLC.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the level of succinic acid impurity is less than about 0.5% (w/w) as measured by HPLC, when stored at 25° C./40% RH for up to 90 days.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the level of succinylmonocholine impurity is less than about 5.0% (w/w) as measured by HPLC, when stored at 25° C./40% RH for up to 90 days.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the level of choline impurity is less than about 3.0% (w/w) as measured by HPLC, when stored at 25° C./40% RH for up to 90 days.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the level of total impurity is less than about 6.0% (w/w) as measured by HPLC, when stored at 25° C./40% RH for up to 90 days.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the level of any unspecified impurity is less than about 0.2% (w/w) as measured by HPLC, when stored at 25° C./40% RH for up to 90 days.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the level of any unidentified impurity is less than about 0.2% (w/w) as measured by HPLC, when stored at 25° C./40% RH for up to 90 days.

In one embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein in said composition upon intravenous or intramuscular administration exhibits bioequivalence to a commercially available reference succinylcholine chloride drug products (such as ANECTIN® and QUELICIN®), and wherein said bioequivalence is established by at least one of: (i) a confidence interval for mean $AUC_{0-t}$ between about 80% and about 125%; (ii) a confidence interval for mean $AUC_{0-infinity}$ between about 80% and about 125%; (iii) a confidence interval for mean $C_{max}$ between about 80% and about 125% or a combination thereof.

In an embodiment, the stable injectable pharmaceutical composition of the invention comprises (a) therapeutically effective amount of succinylcholine chloride; (b) one or more pharmaceutical acceptable solvents; (c) one or more stabilizing agents (e) at least one pH adjusting agent and (f) optionally, one or more additional pharmaceutically acceptable excipients, wherein said composition is free of tonicity contributing agent.

In an embodiment, the stable injectable pharmaceutical composition of the invention comprises (a) succinylcholine chloride at a concentration of 20 mg/mL; (b) water for injection; (c) propylene glycol; and (d) optionally, one or more additional pharmaceutically acceptable excipients.

In another embodiment, the stable injectable pharmaceutical composition of the invention comprises (a) therapeutically effective amount of succinylcholine chloride; (b) water for injection; (c) propylene glycol; and (d) optionally, one or more additional pharmaceutically acceptable excipients; wherein the composition is free of sodium chloride.

In another embodiment, the stable injectable pharmaceutical composition of the invention comprises (a) therapeutically effective amount of succinylcholine chloride; (b) water for injection; (c) propylene glycol; and (d) optionally, one or more additional pharmaceutically acceptable excipients; wherein propylene glycol is present at a concentration of less than about 300 mg/mL.

In an embodiment, the stable injectable pharmaceutical composition of the invention comprises (a) therapeutically effective amount of succinylcholine chloride; (b) water for injection; (c) propylene glycol; (d) polyethylene glycol and (e) optionally, one or more additional pharmaceutically acceptable excipients.

In another embodiment, the stable injectable pharmaceutical composition of the invention comprises (a) therapeutically effective amount of succinylcholine chloride; (b) water for injection; (c) polyethylene glycol and (d) optionally, one or more additional pharmaceutically acceptable excipients, wherein polyethylene glycol is present at a concentration of more than 20 mg/mL.

In another embodiment, the stable injectable pharmaceutical composition of the invention comprises (a) therapeutically effective amount of succinylcholine chloride; (b) water for injection; (c) ethanol and (d) optionally, one or more additional pharmaceutically acceptable excipients, wherein ethanol is present at a concentration of more than 20 mg/mL.

In another embodiment, the stable injectable pharmaceutical composition of the invention comprises (a) therapeutically effective amount of succinylcholine chloride; (b) water for injection; (c) propylene glycol; (d) hydroxypropyl-β-cyclodextrin (HP-β-CD) and/or sulfobutylether-β-cyclodextrin (SBE-β-CD); and (e) optionally, one or more additional pharmaceutically acceptable excipients.

In an embodiment, the stable injectable pharmaceutical composition of the invention comprises (a) therapeutically effective amount of succinylcholine chloride; (b) water for injection; (c) one or more stabilizing agents and (d) optionally, one or more additional pharmaceutically acceptable excipients, wherein molar ratio of succinylcholine chloride to stabilizing agent is from about 0.5:1 to 0.5:50.

In an embodiment of the invention, the stable injectable pharmaceutical composition comprises (a) therapeutically effective amount of succinylcholine chloride; (b) water for injection; (c) one or more stabilizing agents and (d) optionally, one or more additional pharmaceutically acceptable excipients, wherein molar ratio of succinylcholine chloride to stabilizing agent is from about 1:0.5 to 50:1.

In an embodiment, the pharmaceutical composition according to the invention comprises succinylcholine chloride and propylene glycol, wherein molar ratio of succinylcholine chloride to propylene glycol is from 0.5:1 to 0.5:20.

In an embodiment, the pharmaceutical composition according to the invention comprises succinylcholine chloride and polyethylene glycol, wherein molar ratio of succinylcholine chloride to polyethylene glycol is from 1:0.1 to 10:0.1.

In an embodiment, the pharmaceutical composition according to the invention comprises succinylcholine chloride and ethanol, wherein molar ratio of succinylcholine chloride to ethanol is from 1:0.1 to 10:0.1.

The pharmaceutical compositions of the present invention may optionally contain a buffering agent, which is used to resist change in pH upon dilution or addition of acid or alkali. Such compounds include, by way of example and without limitation, succinic acid, sodium dihydrogen phosphate monohydrate, disodium hydrogen phosphate anhydrous, acetic acid, sodium acetate, adipic acid, benzoic acid, sodium benzoate, monobasic sodium phosphate, dibasic sodium phosphate, disodium hydrogen phosphate dodecahydrate, lactic acid, tris buffer, tartaric acid, potassium metaphosphate, potassium phosphate, monobasic sodium acetate, sodium bicarbonate, sodium tartrate and other buffers known to those of ordinary skill in the art.

The pharmaceutical compositions of the present invention may additionally contain a "tonicity contributing agent" that can be used to adjust the tonicity of the liquid formulation. Suitable tonicity contributing agents include lactose, mannitol, dextrose, sodium chloride, sodium sulphate, sorbitol, trehalose, xylitol, sucrose, maltose and other tonicity contributing agents known to those or ordinary skill in the art. In one embodiment, the tonicity of the liquid formulation approximates that of the tonicity of blood or plasma. The amount of tonicity contributing agent may range from about 1 mg/mL to about 50 mg/mL of the composition.

The pharmaceutical compositions of the present invention may additionally contain a chelating agent, which may be selected from the group consisting of ethylene-diaminetetraacetic acid (EDTA), diethylenetriaminepentaacetic acid (DTPA), ethylene glycol-bis (β-aminoethyl ether)-tetra acetic acid (EGTA), N-(hydroxyethyl) ethylene-diaminetriacetic acid (HEDTA), nitrilotriacetic acid (NTA), triethanolamine, 8-hydroxyquinoline, phosphoric acid, gluconic acid, saccharic acid, thiodipropionic acid, acetonic dicarboxylic acid, lecithin, di(hydroxyethyl)glycine, phenylalanine, tryptophan, glycerine, sorbitol and pharmaceutically acceptable salts thereof. In some embodiments, the chelating agent is selected from the group consisting of EDTA, DTPA, phosphoric acid, gluconic acid and a pharmaceutically acceptable salt thereof.

The pharmaceutical compositions of the present invention may additionally contain an antioxidant which inhibits oxidation, and thus is used to prevent the deterioration of preparations by oxidative processes. Such compounds include by way of example and without limitation, acetone, sodium bisulfate, ascorbic acid, ascorbyl palmitate, citric acid, glycine, L-cysteine hydrochloride, L-methionine, butylated hydroxy anisole, butylated hydroxytoluene, hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite and other antioxidants known to those of ordinary skill in the art. The amount of antioxidant may range from about 0.1 mg/mL to about 50 mg/mL of the composition, and preferably from about 0.5 mg/mL to about 25 mg/mL.

The pharmaceutical compositions of the present invention may additionally contain a preservative, which may be selected from the group consisting of benzoic acid, and sodium and potassium salts thereof; sorbic acid, and sodium and potassium salts thereof; chlorobutanol; benzyl alcohol; phenyl ethanol; methyl, ethyl, propyl or butyl-p-hydroxybenzoates; phenol; m-cresol; p-chloro-m-cresol; phenylmercury nitrate; benzalkonium chloride; and mixtures thereof.

The pharmaceutical compositions of the present invention may additionally contain pH adjusting agents. The pH adjusting agents may be selected from the group consisting of hydrochloric acid, sodium hydroxide, potassium hydroxide, magnesium hydroxide, sodium carbonate, tromethamine, sodium linoleate, sodium oleate, potassium carbonate, potassium linoleate, potassium oleate, and mixtures thereof. In one embodiment of the invention, the pharmaceutical composition comprising succinylcholine chloride can be formulated at any suitable pH. The pH of the pharmaceutical composition may range from about 3 to about 5, from about 3.0 to about 4.5, such as about 3.6, when measured at room temperature. In one embodiment of the invention, pharmaceutical composition comprising succinylcholine chloride can be formulated using any suitable pH adjusting agent. In some embodiments, it is possible to maintain the pH of the composition without using a suitable buffering agent.

The pharmaceutical compositions of the present invention may additionally contain anti-foaming agents. The anti-foaming agents may be selected from the group consisting of sodium carboxymethylcellulose, sorbitol, mannitol, polyvinylpyrrolidone (PVP), polyoxyethylene sorbitan monolaurate or monooleate, polysorbates or Tween 20 and 80, polyoxyethylene/polyoxypropylene/polyoxyethylene copolymer (Pluronic L-62), glycerol polyethylene glycol ricinoleate (Cremophor EL), silicone antifoam (Dimethicone), sorbitan monooleate or monolaurate (Span 20 and 80), propylene glycol; polyethylene glycol 300 (PEG), ethanol, dimethyl acetamide (DMA), glycerol, N-methyl-2-pyrrolidone, monothioglycerol, and mixtures thereof.

In another embodiment, the stable injectable pharmaceutical composition of the invention comprising succinylcholine chloride has a viscosity value of about 1 cP (centipoise) to about 5 cP, for example, 1.5 cP, 2 cP, 2.5 cP, 3 cP, 3.5 cP, 4 cP or 4.5 cP.

In another embodiment, the stable injectable pharmaceutical composition comprising succinylcholine chloride according to the present invention has an osmolality value of between about 100 mOsm and about 4000 mOsm, for example, about 100 mOsm, about 150 mOsm, about 200 mOsm, about 250 mOsm, about 300 mOsm, about 350 mOsm, about 400 mOsm, about 450 mOsm, about 500 mOsm, about 550 mOsm, about 600 mOsm, about 650 mOsm, about 700 mOsm, about 750 mOsm, about 800 mOsm, about 850 mOsm, about 900 mOsm, about 950 mOsm, about 1000 mOsm, about 1100 mOsm, about 1150 mOsm, about 1200 mOsm, about 1250 mOsm, about 1300 mOsm, about 1350 mOsm, about 1400 mOsm, about 1450 mOsm, about 1500 mOsm, about 1550 mOsm, about 1600 mOsm, about 1650 mOsm, about 1700 mOsm, about 1750 mOsm, about 1800 mOsm, about 1850 mOsm, about 1900 mOsm, about 1950 mOsm, about 2000 mOsm, about 2200 mOsm, about 2300 mOsm, about 2400 mOsm, about 2500 mOsm, about 2600 mOsm, about 2700 mOsm, about 2800 mOsm, about 2900 mOsm, about 3000 mOsm, about 3100 mOsm, about 3200 mOsm, about 3300 mOsm, about 3400 mOsm, about 3500 mOsm, about 3600 mOsm, about 3700 mOsm, about 3800 mOsm, about 3900 mOsm, or about 4000 mOsm.

In yet another embodiment, the present invention relates to method of using the inventive compositions as an adjunct to general anesthesia, to facilitate tracheal intubation, and to provide skeletal muscle relaxation during surgery or mechanical ventilation in a human subject, the method comprising administering to the human subject the inventive composition comprising succinylcholine chloride, wherein the composition exhibits rapid onset of action and provides faster muscle relaxation.

According to yet another embodiment, the present invention provides stable injectable pharmaceutical composition of succinylcholine chloride at concentrations higher than 5 mg/mL and methods of preparing such solutions. In particular, the present invention provides stable aqueous succinylcholine chloride solutions for parenteral administration at concentrations about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 10.5 mg/mL, about 11 mg/mL, about 11.5 mg/mL, about 12 mg/mL, about 12.5 mg/mL, about 13 mg/mL, about 13.5 mg/mL, about 14 mg/mL, about 14.5 mg/mL, about 15 mg/mL, about 15.5 mg/mL, about 16 mg/mL, about 16.5 mg/mL, about 17 mg/mL, about 17.5 mg/mL, about 18 mg/mL, about 18.5 mg/mL, about 19 mg/mL, about 19.5 mg/mL, about 20 mg/mL, about 20.5 mg/mL, about 21 mg/mL, about 21.5 mg/mL, about 22 mg/mL, about 22.5 mg/mL, about 23 mg/mL, about 23.5 mg/mL, about 24 mg/mL, about 24.5 mg/mL, about 25 mg/mL, about 25.5 mg/mL, about 26 mg/mL, about 26.5 mg/mL, about 27 mg/mL, about 27.5 mg/mL, about 28 mg/mL about 28.5 mg/mL, about 29 mg/mL, about 29.5 mg/mL and about 30 mg/mL.

The unit dose of the succinylcholine chloride will be in the range from about 1 to about 200 mg. Exemplary unit doses of succinylcholine chloride range from 1 mg to 200 mg, including unit dosages of 1 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 40 mg, 42.5 mg, 45 mg, 50 mg, 52.5 mg, 55 mg, 57.5 mg, 60 mg, 62.5 mg, 65 mg, 70 mg, 72.5 mg, 75 mg, 80 mg, 82.5 mg, 85 mg, 87.5 mg, 90 mg, 92.5 mg, 95 mg, 97.5 mg, 100 mg, 102.5 mg, 105 mg, 107.5 mg, 110 mg, 112.5 mg, 115 mg, 117.5 mg, 120 mg, 122.5 mg, 125 mg, 127.5 mg, 130 mg, 132.5 mg, 135 mg, 140 mg, 142.5 mg, 145 mg, 150 mg, 152.5 mg, 155 mg, 157.5 mg, 160 mg, 162.5 mg, 165 mg, 170 mg, 172.5 mg, 175 mg, 180 mg, 182.5 mg, 185 mg, 187.5 mg, 190 mg, 192.5 mg, 195 mg, 197.5 mg and 200 mg, wherein unit dose may be packed in a vial, ampoule, pre-filled syringe, cartridge or auto-injector.

In certain embodiment of the invention, the stable injectable solution comprising therapeutically effective amount of succinylcholine chloride may provide onset of action of less than 2 minutes, for example, less than 1 minute, less than 40 seconds, less than 30 seconds, or less than 20 seconds, when the solution is administered via intravenous or intramuscular route to a human at a succinylcholine chloride dose between about 1 mg and about 300 mg. The solution comprising therapeutically effective amount of succinylcholine chloride of the invention provides immediate availability of the entire dose of succinylcholine chloride in the blood when the solution is administered via intravenous or intramuscular route to a human.

In a further embodiment of the invention, the stable injectable pharmaceutical composition comprising succinylcholine chloride may provide a value of $C_{max}$ of more than 0.5 μg/mL, for example, more than 0.5 μg/mL, more than 1 μg/mL, more than 1.5 μg/mL, more than 2 μg/mL, more than 2.5 μg/mL, more than 3 μg/mL, more than 3.5 μg/mL, more than 4 μg/mL, more than 4.5 μg/mL, more than 5 μg/mL, more than 5.5 μg/mL, more than 6 μg/mL, more than 6.5 μg/mL, more than 7 μg/mL, more than 7.5 μg/mL, more than 8 μg/mL, more than 8.5 μg/mL, more than 9 μg/mL, more than 9.5 μg/mL, more than 10 μg/mL, more than 15 μg/mL, more than 20 μg/mL, more than 25 μg/mL, more than 30 μg/mL, more than 35 μg/mL, more than 40 μg/mL, more than 45 μg/mL, more than 50 μg/mL, more than 55 μg/mL, more than 60 μg/mL, more than 65 μg/mL, more than 70 μg/mL, more than 75 μg/mL, more than 80 μg/mL, more than 85 μg/mL, more than 90 μg/mL, more than 95 μg/mL, or more than 100 μg/mL, when the composition is administered via parenteral route to a subject at a succinylcholine chloride dose of between about 1 mg and about 300 mg.

In a further embodiment, the stable injectable pharmaceutical composition comprising succinylcholine chloride may provide a value of AUC of more than 10 μg*h/mL, more than 20 μg*h/mL, more than 30 μg*h/mL, more than 40 μg*h/mL, more than 50 μg*h/mL, more than 60 μg*h/mL, more than 70 μg*h/mL, more than 80 μg*h/mL, more than 90 μg*h/mL, more than 100 μg*h/mL, more than 150 μg*h/mL, more than 200 μg*h/mL, more than 250 μg*h/mL, more than 300 μg*h/mL, more than 350 μg*h/mL, more than 400 μg*h/mL, more than 450 μg*h/mL, more than 500 μg*h/mL, more than 550 μg*h/mL, more than 600 μg*h/mL, more than 650 μg*h/mL, more than 700 μg*h/mL, more than 750 μg*h/mL, more than 800 μg*h/mL, more than 850 μg*h/mL, more than 900 μg*h/mL, more than 950 μg*h/mL, more than 1000 μg*h/mL, more than 1050 μg*h/mL, more than 1100 μg*h/mL, more than 1150 μg*h/mL, or more than 2000 μg*h/mL, when the composition is administered via parenteral route to a subject at a succinylcholine chloride dose of between about 1 mg and about 300 mg.

In another embodiment, the stable injectable pharmaceutical composition of the invention comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the composition is disposed in a pre-filled syringe or a vial.

In an embodiment of the invention, the stable injectable pharmaceutical composition disposed in a pre-filled syringe comprises; (a) therapeutically effective amount of succinylcholine chloride; (b) one or more pharmaceutically acceptable solvents; (c) one or more stabilizing agents; and (d) optionally, one or more other pharmaceutically acceptable excipients, wherein the composition in said pre-filled syringe is stable at 25° C. for at least 30 days.

In an embodiment of the invention, the stable injectable pharmaceutical composition disposed in a pre-filled syringe comprises; (a) therapeutically effective amount of succinylcholine chloride; (b) one or more pharmaceutically acceptable solvents; (c) one or more stabilizing agents; and (d) optionally, one or more other pharmaceutically acceptable excipients, wherein said composition is free of tonicity contributing agent.

In an embodiment of the invention, the stable injectable pharmaceutical composition disposed in a pre-filled syringe comprises; (a) succinylcholine chloride at a concentration of about 20 mg/mL; (b) purified water; (c) propylene glycol; wherein said composition is free of sodium chloride and wherein the composition in said pre-filled syringe is stable at 25° C. for at least 30 days.

In another embodiment of the invention, the sterile stable injectable pharmaceutical composition comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein the composition is sterilized using aseptic filtration technique.

In another embodiment of the invention, the sterile stable injectable pharmaceutical composition comprises (a) therapeutically effective amount of succinylcholine chloride; (b) one or more pharmaceutically acceptable solvents; (c) one or more stabilizing agents; and (d) optionally, one or more other pharmaceutically acceptable excipients, wherein said composition contains no overage of succinylcholine chloride.

In certain embodiment, the invention relates to methods for making a composition of the invention comprising: (i) dispensing 80% v/v of water for injection; (ii) sequentially adding stabilizing agent and stirring to form solution-1; (iii) adding succinylcholine chloride to solution-1 and stirring to form solution-2; (iv) adjusting the pH of the solution-2 by adding a suitable pH adjusting agent; (v) making up the final volume with remaining water for injection to obtain final solution; (vi) purging the nitrogen gas throughout the procedure; (vii) filtering the final solution; and (viii) filling the solution in syringes or vials and stoppering with coated stoppers.

As used herein, "sterilization" refers to any physical or chemical process which destroys all life forms, with special regard to microorganisms (including bacteria and sporogenous forms), and inactivates viruses.

As used herein, "terminal sterilization" refers to a sterilization process that takes place after that the product to be sterilized has been filled into at least its primary packaging. Terminal sterilization presents the advantage of avoiding further opportunities for contamination of the product due to human intervention.

As used herein, "heat sterilization" refers to a sterilization process achieved by exposing the product to be sterilized to heat. As used herein, "steam sterilization" refers to a sterilization process achieved by exposing the product to be sterilized with saturated steam.

Certain embodiments additionally relate to sterilizing the finished products, e.g., aseptic filtration-filling-sealing, terminal sterilization, incorporation of sterilizing agents, irradiation, and/or heating.

Sterilization may be accomplished by any of the conventional methods including aseptic filling, irradiation and heat sterilization. Heat sterilization is normally performed using steam, preferably wet steam to allow for the use of pressure as a means of temperature control. The time period for the sterilization must be long enough to meet the sterility requirements required of an injectable product. When steam is used, the period may be from about 5 to 30 minutes at temperatures of about 110° C. to 130° C., or from about 10 to 30 minutes at temperatures of about 110° C. to 130° C., or from about 15 to 30 minutes at temperatures of about 120° C. to 125° C. In another embodiment, the sterilization can be performed at 120° C. for 5 to 15 minutes.

A pharmaceutically inert gas may be bubbled into the solution to drive out oxygen, which may be selected from nitrogen or carbon dioxide. Preferably, the solution was kept under nitrogen or carbon dioxide sparging until dissolved oxygen is less than 10 mg/L in the final solution.

Containers suitable according to the present invention are those known in the art and include vials, cartridges, pre-filled syringes, auto-injectors, infusion bags, bottles and ampoule presentations. Containers may be fabricated from glass or from polymeric materials. Suitable containers should be of a size sufficient to hold one or more doses of succinylcholine chloride.

The present invention provides for stable injectable pharmaceutical composition of succinylcholine chloride in single-dose and/or multi-dose compositions. In some embodiments, the composition may be contained in vials or pre-filled syringes. In some embodiments, the vials may be made from clear glass, amber glass, or plastic. In some embodiments, the vials or pre-filled syringes may have a capacity in the range of about 0.1 mL to 100 mL in volume, about 1 mL to 50 mL, about 1 mL to 10 mL, or about 1 mL to 5 mL. In some embodiments, the composition may exist in a 5 mL single-dose pre-filled syringe. In some embodiments, a 5 mL single vial may include a single-dose formulation. In some embodiments, a 10 mL vial may include a single-dose formulation. In some embodiments, the 10 mL vial may have a multi-dose formulation. In some embodiments, the same vial may be used for multiple applications of the composition for up to about 10 days, about 15 days, about 30 days, about 45 days, or about 60 days after initial use.

The polymeric materials which may be used for the pre-filled syringe include: polysulfone, polycarbonate, polypropylene, polyethylene ((low-density polyethylene or high-density polyethylene), ethylene/propylene copolymers, polyolefins, acrylic-imide copolymers, polyester (e.g. polyethylene terephthalate, polyethylene naphthalate and the like), Teflon™, Nylon, acetal (Delrin), polymethylpentene, polyvinylidene chloride, ethylvinylacetate, AN-copolymer etc. In addition, cyclic olefin copolymer (COC), cyclic olefin polymer (COP), crystal zenith (CZ) resin containers and similar resins can be used as rigid containers and syringes.

A pre-filled syringe comprising stable injectable pharmaceutical composition of succinylcholine chloride according to the invention is advantageous, as compared to vials or ampoules. A pre-filled syringe fabricated from a polymer is not only be convenient for handling, storage and administration, but also minimizes mixing or dosing errors. The pre-filled syringe according to the invention may be included in a single use auto injectors and reusable auto injectors. The pre-filled syringe contains various constituent parts, for example, a sterile clear USP Type-I siliconized glass syringe barrel (1 mL, cut flange with a gauge (29 size), hypodermic needle (½ inch) fitted with rigid needle shield and laminated bromobutyl plunger stopper for the barrel.

In a pre-filled syringe, the drug and diluent may be in constant contact with the components like the piston and nozzle cap for months or years. Increasing prevalence of drugs which can bind to the surface of glass surfaces also causes problems in stability. Additionally, glass is breakable and requires more care when filling and handling. Further, the glass pre-filled syringe presents design and manufacturing challenges.

Plastic pre-filled syringe offers a true benefit over glass syringe. Plastic pre-filled syringe provides robustness and is also lightweight, while delivering enough stability. Plastic pre-filled syringes advantageously help improve chemical stability of otherwise relatively labile compounds (e.g., succinylcholine) under refrigerated conditions (about 2° C. to about 8° C., or about 5° C.) and at room temperature (about 25° C.). Further advantages are simple disposal, dosage precision and reduction of medical waste.

Further, pre-filled glass syringes can become clogged and malfunction during the process of connecting them to pin-activated needleless IV access systems. Unfortunately, such failure is not detected until after the syringe is inserted into the pin-activated needleless intravenous access system. For example, the action of inserting the syringe can cause the pin in the access system to clog or break off in the syringe tip, thus preventing delivery of the medication and necessitating placement of a new intravenous access line. As a consequence, USFDA has advised that the use of needleless pre-filled glass syringes in emergency situations should be avoided. Plastic pre-filled syringes provide solution to the problem of clogging or breakage of syringe tip and facilitates administration of succinylcholine safely in Emergency Room (ER) or Operating Room (OR) settings.

In an embodiment, improved stability is contemplated where the inventive succinylcholine composition is stored in a pre-filled plastic syringe at about 2-8° C. or at 25° C. For example, Succinylmonocholine chloride impurity may be present in a range between 0.1-3%, after storing inventive succinylcholine composition in a pre-filled plastic syringe at about 25° C. for 15-60 days or more than 60 days.

In some embodiments, the inventive succinylcholine composition disposed in a pre-filled plastic syringe contains not more than about 6% total impurities after storage at 2-8° C. for at least 2 months, for at least 3 months, at least 6 months, at least 9 months, at least 12 months, at least 15 months, at least 18 months, at least 21 months, at least 24 months, at least 30 months, or at least 36 months as determined by HPLC, and in other embodiments the inventive succinylcholine composition disposed in a pre-filled plastic syringe contains not more than about 5% succinylmonocholine chloride impurity after storage at 2-8° C. for at least 2 months, for at least 3 months, at least 6 months, at least 9 months, at least 12 months, at least 15 months, at least 18 months, at least 21 months, at least 24 months, at least 30 months, or at least 36 months as determined by HPLC. In further embodiments, the inventive succinylcholine composition disposed in the pre-filled plastic syringe contains not more than about 0.5% succinic acid impurity after storage at 2-8° C. for at least 2 months, for at least 3 months, at least 6 months, at least 9 months, at least 12 months, at least 15 months, at least 18 months, at least 21 months, at least 24 months, at least 30 months, or at least 36 months as determined by HPLC. In further embodiments, the inventive succinylcholine composition disposed in the pre-filled plastic syringe contains not more than about 3% choline impurity after storage at 2-8° C. for at least 2 months, for at least 3 months, at least 6 months, at least 9 months, at least 12 months, at least 15 months, at least 18 months, at least 21 months, at least 24 months, at least 30 months, or at least 36 months as determined by HPLC.

In some embodiments, the inventive succinylcholine composition disposed in a pre-filled plastic syringe contains not more than about 6% total impurities after storage at 25° C./60% RH or 25° C./40% RH or at room temperature for at least 2 months, for at least 3 months, at least 6 months, at least 9 months, at least 12 months, at least 15 months, at least 18 months, at least 21 months, at least 24 months, at least 30 months, or at least 36 months as determined by HPLC. In other embodiments, the inventive succinylcholine composition disposed in a pre-filled plastic syringe contains not more than about 5% succinylmonocholine chloride impurity after storage at 25° C./60% RH or 25° C./40% RH or at room temperature for at least 2 months, for at least 3 months, at least 6 months, at least 9 months, at least 12 months, at least 15 months, at least 18 months, at least 21 months, at least 24 months, at least 30 months, or at least 36 months as determined by HPLC. In further embodiments, the inventive succinylcholine composition disposed in the pre-filled plastic syringe contains not more than about 0.5% succinic acid impurity after storage at 25° C./60% RH or 25° C./40% RH or at room temperature for at least 2 months, for at least 3 months, at least 6 months, at least 9 months, at least 12 months, at least 15 months, at least 18 months, at least 21 months, at least 24 months, at least 30 months or at least 36 months as determined by HPLC. In further embodiments, the inventive succinylcholine composition disposed in the pre-filled plastic syringe contains not more than about 3% choline impurity after storage at 25° C./60% RH or 25° C./40% RH or at room temperature for at least 2 months, for at least 3 months, at least 6 months, at least 9 months, at least 12 months, at least 15 months, at least 18 months, at least 21 months, at least 24 months, at least 30 months, or at least 36 months as determined by HPLC.

In an embodiment, the present invention provides a kit comprising an auto injector which contains a pre-filled syringe (a pre-filled syringe assembled/placed in the auto injector). The autoinjector may be integrated with a needle stick protection feature and holds a pre-filled syringe containing a single dose, whereby the entire deliverable volume is expelled.

In an embodiment, a kit comprising a prefilled syringe or syringe cartridge comprising an injectable pharmaceutical composition comprising; (a) therapeutically effective amount of succinylcholine chloride; (b) one or more pharmaceutically acceptable solvents; (c) one or more stabilizing agents; and (d) optionally, one or more other pharmaceutically acceptable excipients, wherein the kit further comprises an injection device for administration of the composition to a subject in need of such pharmaceutical composition and wherein the injection device comprises a needle and the prefilled syringe or syringe cartridge.

The stable injectable succinylcholine chloride solution preparations as described herein may further comprise effective amounts of one or more other therapeutically active ingredient.

Minimizing medication error: Currently, there is no standardized color-coded labelling system in anaesthesia practice that is universally implemented and enforced by accrediting organizations. Inconsistencies in labelling system can lead to misidentification of medication syringes, medication errors, and adverse patient outcomes.

Human error makes up an estimated 80% of medication errors in health care. Anesthesia providers work in high-stress situations and environments. The operating room is a complex environment that presents a multitude of distractions for anesthesia providers. Syringes containing drugs frequently utilized by anesthesia providers are many times instinctually recognized and chosen based on their location and visual features. Recalling and distinguishing an object relies heavily on shape, colour, brightness, and contrast. As these characteristics become increasingly distinct, they become increasingly identifiable. Ubiquitous adoption of a standardized color-coded label on pre-filled syringe is capable of increasing patient safety and decreasing the incidence of mediation errors through the facilitation of syringe recognition by anaesthesia providers in the perioperative period.

The objective of implementing standardized labelling is to improve patient safety by facilitating identification of succinylcholine pre-filled syringes labelled with standardized color-coded medication labels. The label specifications used facilitate to identify succinylcholine pre-filled syringes include the size, color, content, pattern, and type of label used.

In an embodiment, stable pre-filled syringes of the invention with standardized colour-coded medication label suitable for parenteral administration comprises (a) succinylcholine chloride; (b) one or more pharmaceutical acceptable solvents; (c) one or more stabilizing agents (d) one or more tonicity contributing agents; (e) optionally, one or more additional pharmaceutically acceptable excipients, wherein the standardized colour-coded medication label facilitates proper identification of succinylcholine pre-filled syringes in Emergency Room (ER) or Operating Room (OR) settings, thereby increasing patient safety and decreasing the incidence of mediation errors.

Stability: The terms "stable" and "stability" mean that the evolution of the product with time and/or under specific environmental conditions (i.e., temperature, humidity, etc.) has no significant effects on its quality, safety and/or efficacy for a given time period. It can be measured through the formation of degradation products (impurities), variation of pH, appearance (precipitation), microbial growth, and/or color. The term "stable" indicates both chemical and physical stability. The term "stable" further means that no more than about a 10% loss of succinylcholine chloride under typical commercial storage conditions.

Preferably, formulations of the present inventions will have no more than about a 8% loss of succinylcholine chloride, more preferably, no more than about a 5% loss of succinylcholine chloride, more preferably, no more than about a 3% loss of succinylcholine chloride upon storage at room temperature for at least 2 months, for at least 3 months, at least 6 months, at least 9 months, or at least 12 months. Preferably, formulations of the present inventions will have no more than about a 8% loss of succinylcholine chloride, more preferably, no more than about a 5% loss of succinylcholine chloride, more preferably, no more than about a 3% loss of succinylcholine chloride under storage conditions, such as 25° C./60% RH or 25° C./40% RH for at least 2 months, for at least 3 months, at least 6 months, at least 9 months, and at least 12 months. Preferably, formulations of the present inventions will have no more than about a 8% loss of succinylcholine chloride, more preferably, no more than about a 5% loss of succinylcholine chloride, more preferably, no more than about a 3% loss of succinylcholine chloride under storage conditions of 2-8° C. for at least 2 months, for at least 3 months, at least 6 months, at least 9 months, at least 12 months, at least 15 months, at least 18 months, at least 21 months, at least 24 months, at least 30 months and at least 36 months.

In an embodiment, a stable pre-filled plastic syringe suitable for parenteral administration comprises (a) succinylcholine chloride; (b) one or more pharmaceutical acceptable solvents; (c) one or more stabilizing agents and (d) optionally, one or more additional pharmaceutically acceptable excipients, wherein said composition is stable at 2-8° C. for at least 18 months followed by storage at 25° C. for at least 30 days.

In an embodiment, the inventive pharmaceutical compositions are stable for up to 14 days at room temperature without significant loss of potency. In another embodiment, inventive pharmaceutical compositions are stable for at least 1 month at room temperature without significant loss of potency. In yet another embodiment, inventive pharmaceutical compositions are stable for at least 2 months at room temperature without significant loss of potency.

In certain embodiments, the inventive pharmaceutical compositions are stable for at least 1 month when stored at 25° C. and 60% RH or 25° C./40% RH. In certain embodiments, the inventive pharmaceutical compositions are stable for at least 2 months when stored at 25° C. and 60% RH or 25° C./40% RH. In certain embodiments, the inventive pharmaceutical compositions are stable for at least 24 months when stored at 2-8° C.

In particular, the presence of succinylmonocholine (i.e., 2-[(3-carboxypropanoyl)oxy]-N,N,N-trimethylethane-1-aminium) as an impurity may be monitored. The structure of succinylmonocholine is shown below:

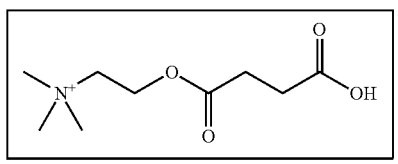

In certain embodiments, the inventive pharmaceutical composition has a level of succinylmonocholine impurity of less than 5%, less than 3%, less than 1%, less than 0.8%, or less than 0.4% as measured by HPLC.

In another embodiment, the stable injectable succinylcholine chloride pharmaceutical composition comprising succinylcholine chloride is clear or free of any crystals/precipitates by visual, inspection after storage for at least 1 month, for example, 2 months, 3 months, 6 months, 12 months, 18 months, or 24 months, at 2-8° C., 25° C./60% RH or 25° C./40% RH conditions. The solution of the present invention provides value of absorbance of not more than 1, for example, not more then 0.75, 0.5, 0.4, 0.3, 0.2, 0.1 or 0.05, and value of % transmittance of not less than 90%, for example, not less than 95%, 96%, 97%, 98%, 99%, 99.5% or 99.9%.

In another embodiment, the stable pharmaceutical composition comprising succinylcholine chloride for parenteral administration does not contain more than 5% of 2-[(3-carboxypropanoyl) oxy]-N,N,N-trimethylethane-1-aminium (also known as succinylmonocholine) impurity, such as less than 3%, 2%, 1%, 0.9%, 0.8%, 0.7%, 0.6%, 0.5%, 0.4%, 0.3%, 0.2% or 0.1%, by weight of succinylcholine chloride, as measured by HPLC.

In another embodiment, the stable pharmaceutical composition comprising succinylcholine chloride for parenteral administration does not contain more than 3% of 2-Hydroxy-N,N,N-trimethylethane-1-aminium (also known as choline) impurity, such as less than 0.9%, 0.8%, 0.7%, 0.6%, 0.5%, 0.4%, 0.3%, 0.2% or 0.1%, by weight of succinylcholine chloride, as measured by HPLC.

In another embodiment, the stable pharmaceutical composition comprising succinylcholine chloride for parenteral administration does not contain more than 0.5% of butanedioic acid (also known as succinic acid) impurity, such as less than 0.9%, 0.8%, 0.7%, 0.6%, 0.5%, 0.4%, 0.3%, 0.2% or 0.1%, by weight of succinylcholine chloride, as measured by HPLC.

In another embodiment, the shelf-life of a stable injectable composition of the invention comprising succinylcholine chloride, when stored at 2-8° C. in the sealed original packaging, may be between 1 month and 36 months, between 6 months and 24 months, or between 12 months and 18 months.

Dosage and Administration: The inventive pharmaceutical compositions as described herein may be used as an adjunct to general anesthesia, to facilitate tracheal intubation, or to provide skeletal muscle relaxation during surgery or mechanical ventilation in which therapeutically effective amount of succinylcholine chloride is administered to a human subject.

Preferably, the present application relates to method of using the inventive compositions as an adjunct to general anesthesia, to facilitate tracheal intubation, and to provide skeletal muscle relaxation during surgery or mechanical ventilation, the method comprising administering the inventive composition comprising succinylcholine chloride to the human subject.

For short surgical procedures in adults, recommended optimum dose varies among individuals and may be from 0.3 to 1.1 mg/kg succinylcholine chloride injection given intravenously to produce neuromuscular blockade and to facilitate tracheal intubation. For long surgical procedures, the dose of succinylcholine chloride administered by infusion depends upon the duration of the surgical procedure and the need for muscle relaxation. The average rate for an adult range between 2.5 and 4.3 mg per minute.

In an embodiment, the present invention relates to facilitating tracheal intubation in a human subject, the method comprising administering 0.3 to 1.1 mg/kg succinylcholine chloride given as intravenous bolus injection to a human subject.

In one embodiment of the method as disclosed herein, the intravenous (IV) bolus dose of succinylcholine chloride is administered to the patient over the course of about 30 seconds to about 6 minutes, including all values and subranges there between. The IV dose of succinylcholine chloride may be administered to a patient in about 30 seconds, about 31 second, about 32 seconds, about 33 seconds, about 34 seconds, about 35 second, about 36 seconds, about 37 seconds, about 38 seconds, about 39 second, about 40 seconds, about 41 second, about 42 seconds, about 43 seconds, about 44 seconds, about 45 second, about 46 seconds, about 47 seconds, about 48 seconds, about 49 second, about 50 seconds, about 51 second, about 52 seconds, about 53 seconds, about 54 seconds, about 55 second, about 56 seconds, about 57 seconds, about 58 seconds, about 59 second, about 1 minute, about 2 minute, about 3 minute, about 4 minute, about 5 minute, about 6 minute or any ranges between these values.

In one embodiment, the dose of succinylcholine chloride is in the range of from about 0.3 mg to about 300 mg.

In some embodiments, the methods comprise administering stable injectable succinylcholine chloride solution to a subject for a duration of about 30 seconds, about 45 seconds, about 1 minute, about 2 minutes, about 4 minutes, about 6 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, about 10 hours, about 11 hours, or about 12 hours.

In one embodiment, the methods disclosed herein comprise administering to the patient a dose of succinylcholine chloride intravenously or intramuscularly, wherein the succinylcholine chloride is administered at a dose of about 0.3 mg to 300 mg. In some embodiments, the methods disclosed herein comprise administering to the patient a dose of succinylcholine chloride intravenously or intramuscularly, wherein the succinylcholine chloride is at a concentration of about 1 mg/mL or 200 mg/mL. In one embodiment, the intravenous dose is a bolus dose or an infusion.

In an embodiment, the present invention relates to a method for facilitating tracheal intubation in adult patients with intravenous dose of succinylcholine chloride ranging from 0.3 mg/kg a day to 1.1 mg/kg.

In an embodiment, the present invention relates to methods for providing muscle relaxation in adult patients with intravenous infusion dose of succinylcholine chloride ranging between 2.5 and 4.3 mg per minute.

In an embodiment, the present invention relates to methods for facilitating tracheal intubation in pediatric patients with intravenous dose of succinylcholine chloride ranging from 1 mg/kg a day to 2 mg/kg.

In an embodiment, the present invention relates to a method for providing muscle relaxation in pediatric patients with intramuscular dose of succinylcholine chloride ranging from 3 mg/kg a day to 4 mg/kg.

In certain embodiment, the inventive pharmaceutical compositions described herein may be used to treat adults and adolescents (e.g., about 13-17 years). In certain embodiment, the pharmaceutical compositions described herein may be used as monotherapy or as adjunctive therapy. For example, additional active agents may be used in adjunctive therapy with succinylcholine chloride, such as opioid medications (e.g., morphine, hydromorphone, etc.).

The dosage levels can be dependent on the nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

HPLC procedure: As explained in detail below, the following HPLC procedure was used to detect, quantify impurities of succinylcholine and to determine assay % of succinylcholine. The materials and methods are listed below:

TABLE 1

Related substances identification by HPLC Chromatographic conditions

| | |
|---|---|
| Column | Pursuit XRs C18, 250 mm × 4.6 mm, 5μ |
| Column Temperature | 50° C. |
| Flow rate | 0.8 mL/min |
| Detector | 214 nm with UV detector |
| Injection volume | 15 μL |
| Run time | 80 minutes for blank and samples |
| Sample temperature | 10° C. |
| Mode of elution | Gradient |
| Preparation of Buffer | Weigh and transfer about 3.85 g of 1-Pentane sulphonic acid sodium salt anhydrous and 2.76 g of Sodium dihydrogen phosphate monohydrate into a beaker containing 1000 mL of water and sonicate to dissolve. To this add 1 mL of Orthophosphoric acid and mix well. Filter the buffer through 0.45μ membrane filter. |
| Preparation of Organic modifier | Mix Acetonitrile, Methanol and Water in the ratio of 50:40:10 (% v/v/v) respectively |
| Preparation of Mobile Phase A | Prepare a mixture of Buffer and Organic modifier in the ratio of 95:5 (% v/v) and degas it for about 10 minutes. |
| Preparation of Mobile Phase B | Prepare a mixture of Buffer and Organic modifier in the ratio of 30:70 (% v/v) and degas it for about 10 minutes. |

TABLE 2

Gradient program

| Time (mins) | % Mobile phase-A | % Mobile phase-B |
|---|---|---|
| 0 | 100 | 0 |
| 5 | 100 | 0 |
| 55 | 50 | 50 |
| 57 | 0 | 100 |
| 65 | 0 | 100 |
| 67 | 100 | 0 |
| 80 | 100 | 0 |

TABLE 3

Choline content identification by HPLC Chromatographic conditions

| | |
|---|---|
| Column | Shodex ® YS-50, 125 * 4.6 mm, 5 uM |
| Column Temperature | 35° C. |
| Flow rate | 1.0 mL/min |
| Injection volume | 30 μL |
| Run time | 30 minutes |
| Sample temperature | 15° C. |
| Mode of elution | Isocratic |
| Mobile Phase | Formic acid |

TABLE 4

Assay of Succinylcholine chloride injection by HPLC Chromatographic conditions

| | |
|---|---|
| Column | Zorbax RX-SIL, 250 mm × 4.6 mm, 5 μm (Part. No.: AG880975-901) or equivalent |
| Column Temperature | 25° C. |
| Flow rate | 0.75 mL/min |
| Detector | 214 nm with UV detector |
| Injection volume | 50 μL |
| Run time | 20 minutes |
| Sample temperature | 10° C. |
| Mode of elution | Isocratic |
| Preparation of Mobile Phase | Mix 1N tetramethylammonium chloride and Methanol in the ratio of 10:90 (v/v) respectively. Filter the mobile phase using 0.45μ membrane filter. Adjust the pH of the solution to 3.0 ± 0.05 using 1N hydrochloric acid and mix well. |

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Example 1

Succinylcholine chloride compositions are set forth in Table 5, 6, 7, 8 and 9.

TABLE 5

| Ingredients (mg/mL) | Composition | | | | | | | | |
|---|---|---|---|---|---|---|---|---|---|
| | 1 | 2 | 3 | 4 | 5 | 6 | 7 | 8 | 9 |
| Succinylcholine chloride | 20 | 20 | 20 | 20 | 20 | 20 | 20 | 20 | 20 |
| Sodium chloride | 4.6 | 4.6 | 4.6 | 4.6 | 4.6 | 4.6 | 4.6 | 4.6 | 4.6 |
| Methyl Paraben | 1.8 | — | — | — | — | — | — | — | — |
| Propyl Paraben | 0.2 | — | — | — | — | — | — | — | — |
| Maleic acid | — | 0.1 | — | — | — | — | — | — | — |
| Tartaric acid | — | — | 0.4 | — | — | — | — | — | — |
| L-Glutamic acid | — | — | — | 2.0 | — | — | — | — | — |
| L-Aspartic acid | — | — | — | — | 2.0 | — | — | — | — |
| Propylene glycol | — | — | — | — | — | 100 | 300 | — | — |
| PEG-300 | — | — | — | — | — | — | — | 100 | — |
| PEG-400 | — | — | — | — | — | — | — | — | 200 |
| Hydrochloric acid | q.s. for adjusting pH 3.5 | | | | | | | | |
| Sodium hydroxide | q.s. for adjusting pH 3.5 | | | | | | | | |
| Water for injection | q.s. to 1 mL | | | | | | | | |

TABLE 6

| Ingredients (mg/mL) | Composition | | | | | | | | | |
|---|---|---|---|---|---|---|---|---|---|---|
| | 10 | 11 | 12 | 13 | 14 | 15 | 16 | 17 | 18 | 19 |
| Succinylcholine chloride | 20 | 10 | 20 | 10 | 20 | 20 | 20 | 20 | 20 | 20 |
| Propylene glycol | 300 | 300 | 300 | 300 | 300 | 100 | 100 | 100 | 100 | 100 |
| Sodium chloride | 4.6 | 4.6 | 4.6 | 4.6 | 4.6 | — | — | — | — | — |
| SBE-β-CD | 160 | 160 | — | — | — | — | — | — | — | — |
| HP-β-CD | — | — | 170 | 170 | 110 | — | — | — | — | — |
| Maleic acid | — | — | — | — | — | — | — | 0.1 | — | — |
| Tartaric acid | — | — | — | — | — | — | — | — | 0.4 | — |
| Glutamic acid | — | — | — | — | — | — | — | — | — | 2 |
| Hydrochloric acid | q.s. for adjusting pH 3.5 | | | | | q.s. for adjusting pH 3.8 | q.s. for adjusting pH 4.3 | | | |
| Sodium hydroxide | q.s. for adjusting pH 3.5 | | | | | q.s. for adjusting pH 3.8 | q.s. for adjusting pH 4.3 | | | |
| Water for injection | q.s. to 1 mL | | | | | | | | | |

TABLE 7

| Ingredients (mg/mL) | Composition | | | | | | | | |
|---|---|---|---|---|---|---|---|---|---|
| | 20 | 21 | 22 | 23 | 24 | 25 | 26 | 27 | 28 |
| Succinylcholine chloride | 20 | 20 | 20 | 20 | 20 | 20 | 20 | 20 | 20 |
| Maleic acid | 0.1 | — | — | — | — | 0.1 | — | — | 0.1 |
| Tartaric acid | — | 0.4 | — | — | — | — | 0.4 | — | — |
| Glutamic acid | — | — | 2 | — | — | — | — | 2 | — |
| SBE-β-CD | — | — | — | 170 | — | 170 | 170 | 170 | 170 |
| HP-β-CD | — | — | — | — | 170 | — | — | — | — |
| PEG-300 | 100 | 100 | 100 | — | — | — | — | — | — |
| Propylene glycol | — | — | — | 100 | 100 | — | — | — | 100 |
| Hydrochloric acid | q.s. for adjusting pH 4.3 | | | | | | | | |
| Sodium hydroxide | q.s. for adjusting pH 4.3 | | | | | | | | |
| Water for injection | q.s. to 1 mL | | | | | | | | |

TABLE 8

| Ingredients (mg/mL) | Composition | | | | | | | |
|---|---|---|---|---|---|---|---|---|
| | 29 | 30 | 31 | 32 | 33 | 34 | 35 | 36 |
| Succinylcholine chloride | 20 | 20 | 20 | 20 | 20 | 20 | 20 | 20 |
| Maleic acid | 0.1 | 0.1 | — | — | — | — | — | — |
| Tartaric acid | — | — | 0.4 | — | — | — | — | — |
| Glutamic acid | — | — | — | 2 | — | — | — | — |
| HP-β-CD | 170 | 170 | 170 | 170 | 100 | 170 | 200 | 250 |
| Propylene glycol | 100 | — | — | — | — | — | — | — |
| Hydrochloric acid | q.s. for adjusting pH 4.3 | | | | q.s. for adjusting pH 4.0 | | | |
| Sodium hydroxide | q.s. for adjusting pH 4.3 | | | | q.s. for adjusting pH 4.0 | | | |
| Water for injection | q.s. to 1 mL | | | | | | | |

TABLE 9

| Ingredients (mg/mL) | Composition | | | | | | | |
|---|---|---|---|---|---|---|---|---|
| | 37 | 38 | 39 | 40 | 41 | 42 | 43 | 44 |
| Succinylcholine chloride | 20 | 20 | 20 | 20 | 20 | 20 | 20 | 20 |
| Sodium chloride | 4.6 | 4.6 | 4.6 | 4.6 | 4.6 | 4.6 | 4.6 | 4.6 |
| Maleic acid | 0.05 | — | — | — | — | — | 0.1 | — |
| Tartaric acid | — | 0.1 | 0.2 | — | — | — | — | — |
| Glutamic acid | — | — | — | 0.5 | 1 | — | — | — |
| HP-β-CD | — | — | — | — | — | — | — | 50 |
| Propylene glycol | — | — | — | — | — | 20 | 20 | — |
| Hydrochloric acid | q.s. for adjusting pH 3.6-3.7 | | | | | | | |
| Sodium hydroxide | q.s. for adjusting pH 3.6-3.7 | | | | | | | |
| Water for injection | q.s. to 1 mL | | | | | | | |

TABLE 10

| Ingredients (mg/mL) | Composition | | | | | |
|---|---|---|---|---|---|---|
| | A | B | C | D | E | F |
| Succinylcholine chloride | 20 | 20 | 20 | 20 | 20 | 20 |
| Propylene glycol | 300 | 250 | 200 | 150 | 100 | 50 |
| Hydrochloric acid | q.s. for adjusting pH 3.6-3.7 | | | | | |
| Sodium hydroxide | q.s. for adjusting pH 3.6-3.7 | | | | | |
| Water for injection | q.s. to 1 mL | | | | | |

TABLE 11

| Ingredients (mg/mL) | Composition | | | | | | |
|---|---|---|---|---|---|---|---|
| | G | H | I | J | K | L | M |
| Succinylcholine chloride | 20 | 20 | 20 | 20 | 20 | 20 | 20 |
| Propylene glycol | 100 | 300 | — | 50 | — | 150 | — |
| Polyethylene glycol 300 | — | — | — | 150 | — | — | 50 |
| Ethanol | — | — | — | — | 120 | 120 | 120 |
| Sodium Chloride | 4.6 | 4.6 | 4.6 | — | — | — | — |
| Hydrochloric acid | q.s. for adjusting pH 3.6-3.7 | | | | | | |
| Sodium hydroxide | q.s. for adjusting pH 3.6-3.7 | | | | | | |
| Water for injection | q.s. to 1 mL | | | | | | |

Manufacturing Procedure of Compositions Set Forth in Table 5, 6, 7, 8, 9, 10 and 11 is as Follows:

Required quantity of water for injection (WFI) was added to manufacturing container and cooled it to 2-8° C. To decrease dissolved oxygen (DO) content in WFI to below 1 ppm, nitrogen gas purging through 0.2 micron filter was initiated. Under continuous nitrogen gas purging, stabilizing agent was sequentially added at a predetermined quantity (as set forth in Table 5, 6, 7, 8, 9, 10 and 11) to WFI and completely dissolved to prepare a solution. Accurately weighed quantity of succinylcholine chloride was added to above solution and stirred under continuous nitrogen gas purging until complete dissolution. The pH of the solution was measured, and an appropriate amount of pH adjusting agent was added to the above solution to adjust pH to predetermined range (as set forth in Table 5, 6, 7, 8, 9, 10 and 11). Under continuous nitrogen gas purging, sufficient quantity of cooled WFI was added to make up volume of solution to final composition. The pH of final composition was measured. Final composition was filtered using sterilizing grade 0.2 micron filter and collected under nitrogen gas blanketing at 2-8° C. Syringes or vials were filled with required volume of final composition and stopped using coated stoppers to obtain pre-filled syringes or vials which were stored at 2-8° C. Entire manufacturing procedure was performed at 2-8° C.

Stability data of Compositions were set forth in below Tables.

TABLE 12

| | Composition 1 | | | |
|---|---|---|---|---|
| Storage Condition | Initial | 25° C./ 60% RH | 25° C./ 40% RH | 2-8° C. |
| Duration | | 1 month | | |
| Pack (MOC) | — | Glass vial | PFS (COC) | PFS (COC) |
| Description | Clear, colorless solution free from visible particles | | | |
| pH | 3.7 | 3.33 | 3.42 | NA |
| Assay (Succinylcholine chloride) | 101.4 | 97.9 | 96.5 | 99.8 |
| Osmolality (mOsmol/kg) | 296 | 298 | 297 | NA |
| Impurities (% w/w) | | | | |
| Succinic acid | 0.084 | 0.042 | 0.044 | 0.005 |
| Succinylmonocholine | 0.212 | 1.689 | 1.715 | 0.43 |

TABLE 12-continued

| Storage Condition | Composition 1 | | | |
|---|---|---|---|---|
| | Initial | 25° C./60% RH | 25° C./40% RH | 2-8° C. |
| Choline | 0.36 | 1.07 | 0.94 | NP |
| Total impurities | 0.32 | 1.94 | 1.97 | 0.65 |

*W = Week/s;
M = Month/s;
MOC: Material of construction;
PFS: prefilled syringe;
COC: cyclic olefin copolymer;
NA: Not Applicable;
NP: Not performed;
ND: Not detected;
CZ: crystal zenith

TABLE 13

| | Composition 2 | | | |
|---|---|---|---|---|
| Storage Condition | Initial | 25° C./60% RH | 25° C./40% RH | 2-8 °C |
| Duration | | 1 month | | |
| Pack (MOC) | | Glass vial | PFS (COC) | PFS (COC) |
| Description | Clear, colorless solution free from visible particles | | | |
| pH | 3.68 | 3.35 | 3.31 | 3.49 |
| Assay (Succinylcholine chloride) | 101 | 98.7 | 96.9 | 100.1 |
| Osmolality (mOsmol/kg) | 285 | 286 | 285 | 284 |
| Impurities (% w/w) | | | | |
| Succinic acid | 0.068 | 0.039 | 0.042 | 0.002 |
| Succinylmonocholine | 0.236 | 1.623 | 1.683 | 0.434 |
| Choline | — | 1.01 | 1.08 | 0.38 |
| Total impurities | 0.3 | 1.66 | 1.86 | 0.44 |

TABLE 14

| | Composition 3 | | | |
|---|---|---|---|---|
| Storage Condition | Initial | 25° C./60% RH | 25° C./40% RH | 2-8° C. |
| Duration | | 1 month | | |
| Pack (MOC) | | Glass vial | PFS (COC) | PFS (COC) |
| Description | Clear, colorless solution free from visible particles | | | |
| pH | 3.51 | 3.35 | 3.35 | 3.41 |
| Assay (Succinylcholine chloride) | 101.40 | 97.0 | 95.6 | 99.7 |
| Osmolality (mOsmol/kg) | 289 | 288 | 289 | 288 |

TABLE 14-continued

| | Composition 3 | | | |
|---|---|---|---|---|
| Storage Condition | Initial | 25° C./60% RH | 25° C./40% RH | 2-8° C. |
| Impurities (% w/w) | | | | |
| Succinic acid | 0.07 | 0.044 | 0.013 | 0.003 |
| Succinylmonocholine | 0.251 | 1.745 | 1.765 | 0.48 |
| Choline | 0.41 | 1.08 | 1.01 | 0.36 |
| Total impurities | 0.49 | 2.18 | 2.17 | 0.89 |

TABLE 15

| | Composition 4 | | | |
|---|---|---|---|---|
| Storage Condition | Initial | 25° C./60% RH | 25° C./40% RH | 2-8° C. |
| Duration | | 1 month | | |
| Pack (MOC) | | Glass vial | PFS (COC) | PFS (COC) |
| Description | Clear, colorless solution free from visible particles | | | |
| pH | 3.50 | 3.38 | 3.38 | 3.42 |
| Assay (Succinylcholine chloride) | 101.4 | 97.7 | 96.2 | 98.9 |
| Osmolality (mOsmol/kg) | 301 | 302 | 302 | 301 |
| Impurities (% w/w) | | | | |
| Succinic acid | 0.07 | 0.045 | 0.043 | 0.006 |
| Succinylmonocholine | 0.238 | 1.864 | 1.866 | 0.472 |
| Choline | NP | 1.14 | 1.14 | 0.4 |
| Total impurities | 0.33 | 2.19 | 2.20 | 0.77 |

TABLE 16

| | Composition 5 | | | |
|---|---|---|---|---|
| Storage Condition | Initial | 25° C./60% RH | 25° C./40% RH | 2-8° C. |
| Duration | | 1 month | | |
| Pack (MOC) | | Glass vial | PFS (COC) | PFS (COC) |
| Description | Clear, colorless solution free from visible particles | | | |
| pH | 3.48 | 3.38 | 3.39 | 3.41 |
| Assay (Succinylcholine chloride) | 100.1 | 96.5 | 97.1 | 100.1 |
| Osmolality (mOsmol/kg) | 305 | 305 | 305 | 304 |
| Impurities (% w/w) | | | | |
| Succinic acid | 0.071 | 0.048 | 0.013 | 0.003 |
| Succinylmonocholine | 0.274 | 1.962 | 1.984 | 0.517 |
| Choline | NP | 1.27 | 1.23 | 0.42 |
| Total impurities | 0.35 | 2.01 | 2.00 | 0.52 |

TABLE 17

| | Composition 6 | | | | | |
|---|---|---|---|---|---|---|
| Storage Condition | Initial | 25° C./60% RH | | | 25° C./40% RH | 2-8° C. |
| Duration | | 1 month | | | | |
| Pack (MOC) | | Glass vial | CZ vial | PFS (COC) | Glass vial | CZ vial | PFS (COC) |
| Description | Clear, colorless solution free from visible particles | | | | | |
| pH | 3.6 | 3.41 | 3.37 | 3.42 | 3.65 | 3.57 | 3.64 |
| Assay (Succinylcholine chloride) | 100.1 | 97.4 | 96.3 | 96.5 | 99.0 | 99.2 | 99.0 |

TABLE 17-continued

| | | Composition 6 | | | | | |
|---|---|---|---|---|---|---|---|
| Storage Condition | Initial | 25° C./ 60% RH | 25° C./ 40% RH | | 2-8° C. | | |
| | | Impurities (% w/w) | | | | | |
| Succinic acid | 0.096 | 0.036 | 0.038 | 0.036 | 0.003 | 0.002 | 0.004 |
| Succinylmonocholine | 0.219 | 1.457 | 1.458 | 1.456 | 0.424 | 0.435 | 0.421 |
| Choline | NP | NP | NP | 0.99 | NP | NP | NP |
| Total impurities | 0.32 | 1.69 | 1.70 | 2.01 | 0.60 | 0.91 | 0.66 |

TABLE 18

| | | Composition 7 | | | | | |
|---|---|---|---|---|---|---|---|
| Storage Condition | Initial | 25° C./ 60% RH | 25° C./ 40% RH | | 2-8° C. | | |
| Duration | | | | 1 month | | | |
| Pack (MOC) | — | Glass vial | CZ vial | PFS (COC) | Glass vial | CZ vial | PFS (COC) |
| Description | | Clear, colorless solution free from visible particles | | | | | |
| pH | 3.57 | 3.45 | 3.41 | 3.50 | 3.47 | 3.56 | 3.78 |
| Assay (Succinylcholine chloride) | 99.4 | 96.1 | 95.4 | 96.9 | 96.8 | 96.8 | 97.1 |
| | | Impurities (% w/w) | | | | | |
| Succinic acid | ND | 0.025 | 0.026 | 0.024 | 0.002 | 0.006 | 0.003 |
| Succinylmonocholine | 0.166 | 1.079 | 1.096 | 1.065 | 0.356 | 0.36 | 0.364 |
| Choline | NP | NP | NP | 0.65 | NP | NP | NP |
| Total impurities | 0.17 | 1.36 | 1.39 | 1.31 | 0.58 | 0.66 | 0.57 |

TABLE 19

| | | Composition 8 | | | | | |
|---|---|---|---|---|---|---|---|
| Storage Condition | Initial | 25° C./ 60% RH | 25° C./ 40% RH | | 2-8° C. | | |
| Duration | | | | 1 month | | | |
| Pack (MOC) | | Glass vial | CZ vial | PFS (COC) | Glass vial | CZ vial | PFS (COC) |
| Description | | Clear, colorless solution free from visible particles | | | | | |
| pH | 3.44 | 3.01 | 3.02 | 3.05 | 3.16 | 3.11 | 3.18 |
| Assay (Succinylcholine chloride) | 101.2 | 96.1 | 96.7 | 96.8 | 98.6 | 99.1 | 99.4 |
| | | Impurities (% w/w) | | | | | |
| Succinic acid | ND | 0.054 | 0.058 | 0.051 | 0.013 | 0.016 | 0.011 |
| Succinylmonocholine | 0.366 | 2.047 | 2.21 | 2.095 | 0.506 | 0.529 | 0.494 |
| Choline | 0.35 | NP | NP | 1.27 | 0.42 | 0.39 | 0.39 |
| Total impurities | 0.37 | 2.28 | 2.29 | 2.30 | 0.60 | 0.73 | 0.67 |

TABLE 20

| | | Composition 9 | | | | | |
|---|---|---|---|---|---|---|---|
| Storage Condition | Initial | 25° C./ 60% RH | 25° C./ 40% RH | | 2-8° C. | | |
| Duration | | | | 1 month | | | |
| Pack (MOC) | | Glass vial | CZ vial | PFS (COC) | Glass vial | CZ vial | PFS (COC) |
| Description | | Clear, colorless solution free from visible particles | | | | | |
| pH | 3.39 | 3.00 | 2.99 | 3.01 | 3.10 | 3.08 | 3.10 |

TABLE 20-continued

| | | Composition 9 | | | | | |
|---|---|---|---|---|---|---|---|
| Storage Condition | Initial | 25° C./60% RH | 25° C./40% RH | | 2-8° C. | | |
| Assay (Succinylcholine chloride) | 100.6 | 96.3 | 95.4 | 95.3 | 99.1 | 97.3 | 98.3 |
| | | Impurities (% w/w) | | | | | |
| Succinic acid | ND | 0.043 | 0.046 | 0.048 | 0.007 | ND | 0.002 |
| Succinylmonocholine | 0.3 | 2.245 | 2.248 | 2.188 | 0.583 | 0.586 | 0.575 |
| Choline | 0.41 | NP | NP | 1.37 | 0.42 | 0.4 | 0.37 |
| Total impurities | 0.3 | 2.29 | 2.29 | 2.28 | 0.61 | 0.59 | 0.58 |

TABLE 21

| | Composition 10 | | | |
|---|---|---|---|---|
| Storage Condition | Initial | 25° C./60% RH | | |
| Duration | | 1 month | | |
| Pack (MOC) | | Glass vial | CZ vial | Amber vial |
| Description | Clear, colorless solution free from visible particles | | | |
| pH | 3.55 | 3.42 | 3.40 | 3.43 |
| Assay (Succinylcholine chloride) | 97.7 | 93.0 | 93.8 | 93.6 |
| Osmolality (mOsmol/kg) | 1112/5560 | 1067*/5335 | 1077*/5385 | 1103*/5515 |
| | Impurities (% w/w) | | | |
| Succinic acid | 0.045 | 0.051 | 0.062 | 0.058 |
| Succinylmonocholine | 0.025 | 1.682 | 1.749 | 1.655 |
| Choline | 0.29 | NP | NP | NP |
| Total impurities | 0.07 | 1.78 | 1.85 | 1.76 |

TABLE 22

| | Composition 10 | | | | |
|---|---|---|---|---|---|
| Storage Condition | 25° C./40% RH | | 2-8° C. | | |
| Duration | | | 1 month | | |
| Pack (MOC) | PFS (COC) | Glass vial | CZ vial | Amber vial | PFS (COC) |
| Description | Clear, colorless solution free from visible particles | | | | |
| pH | 3.46 | 3.63 | 3.50 | 3.51 | 3.51 |
| Assay (Succinylcholine chloride) | 94.6 | 96.5 | 97.1 | 96.0 | 96.3 |
| Osmolality (mOsmol/kg) | 1083*/5415 | 1058*/5290 | 1082*/5410 | 1093*/5465 | 1068*/5340 |
| | Impurities (% w/w) | | | | |
| Succinic acid | 0.048 | 0.029 | 0.024 | 0.024 | 0.023 |
| Succinylmonocholine | 1.594 | 0.370 | 0.416 | 0.354 | 0.390 |
| Choline | NP | NP | NP | NP | NP |
| Total impurities | 1.70 | 0.47 | 0.51 | 0.44 | 0.47 |

TABLE 23

| | Composition 11 | | |
|---|---|---|---|
| Storage Condition | Initial | 25° C./60% RH | 2-8° C. |
| Duration | | 1 month | |
| Pack (MOC) | | Glass vial | Glass vial |
| Description | Clear, colorless solution free from visible particles | | |
| pH | 3.6 | 3.47 | 3.48 |
| Assay (Succinylcholine chloride) | 98 | 96.5 | 98.7 |
| Osmolality (mOsmol/kg) | 1072/5360 | NP | NP |
| | Impurities (% w/w) | | |
| Succinic acid | ND | 0.001 | ND |
| Succinylmonocholine | ND | 1.729 | 0.449 |
| Choline | 0.32 | NP | NP |
| Total impurities | 0.32 | 1.74 | 0.46 |

TABLE 24

| | Composition 12 | | | |
|---|---|---|---|---|
| Storage Condition | Initial | 25° C./60% RH | | |
| Duration | | 1 month | | |
| Pack (MOC) | | Glass vial | CZ vial | Amber vial |
| Description | Clear, colorless solution free from visible particles | | | |
| pH | 3.5 | 3.44 | 3.46 | 3.42 |
| Assay (Succinylcholine chloride) | 99.8 | 97.0 | 97.2 | 97.4 |
| Osmolality (mOsmol/kg) | 1023/5115 | NP | NP | NP |
| | Impurities (% w/w) | | | |
| Succinic acid | ND | 0.012 | 0.014 | 0.01 |
| Succinylmonocholine | 0.025 | 0.945 | 0.964 | 0.928 |
| Choline | NP | NP | NP | NP |
| Total impurities | 0.03 | 1.13 | 1.15 | 1.11 |

TABLE 25

| | Composition 12 | | | | |
|---|---|---|---|---|---|
| Storage Condition | 25° C./40% RH | | 2-8° C. | | |
| Duration | | | 1 month | | |
| Pack (MOC) | PFS (COC) | Glass vial | CZ vial | Amber vial | PFS (COC) |
| Description | Clear, colorless solution free from visible particles | | | | |
| pH | 3.49 | 3.45 | 3.44 | 3.44 | 3.52 |

TABLE 25-continued

| | Composition 12 | | | | |
|---|---|---|---|---|---|
| Storage Condition | 25° C./ 40% RH | | 2-8° C. | | |
| Assay (Succinylcholine chloride) | 97.3 | 98.1 | 97.7 | 97.5 | 97.5 |
| | Impurities (% w/w) | | | | |
| Succinic acid | 0.012 | ND | ND | 0.003 | ND |
| Succinyl-monocholine | 0.885 | 0.219 | 0.223 | 0.237 | 0.228 |
| Choline | NP | NP | NP | NP | NP |
| Total impurities | 1.04 | 0.59 | 0.51 | 0.90 | 0.39 |

TABLE 26

| | Composition 13 | | |
|---|---|---|---|
| Storage Condition | Initial | 25° C./ 60% RH | 2-8° C. |
| Duration | | 1M | |
| Pack (MOC) | | Glass vial | Glass vial |
| Description | Clear, colorless solution free from visible particles | | |
| pH | 3.57 | 3.5 | 3.63 |
| Assay (Succinylcholine chloride) | 96.7 | 96.8 | 98.7 |
| Osmolality (mOsmol/kg) | 991/ 4955 | NP | NP |
| | Impurities (% w/w) | | |
| Succinic acid | 0.021 | 0.041 | 0.019 |
| Succinylmonocholine | 0.052 | 1.106 | 0.204 |
| Choline | 0.13 | NP | NP |
| Total impurities | 0.07 | 1.38 | 0.45 |

TABLE 27

| | Composition 14 | | | | | |
|---|---|---|---|---|---|---|
| Storage Condition | 25° C./60% RH | | | 2-8° C. | | |
| Duration | 1 month | | | 1 month | | |
| Pack (MOC) | Glass vial | CZ vial | Amber vial | Glass vial | CZ vial | Amber vial |
| Description | Clear, colorless solution free from visible particles | | | | | |
| pH | 3.45 | 3.41 | 3.44 | 3.52 | 3.49 | 3.54 |
| Assay (Succinylcholine chloride) | 96.2 | 95.5 | 95.7 | 97.8 | 97.6 | 97.0 |
| | Impurities (% w/w) | | | | | |
| Succinic acid | 0.013 | 0.007 | 0.011 | 0.003 | 0.007 | 0.005 |
| Succinylmonocholine | 0.973 | 0.994 | 0.978 | 0.219 | 0.208 | 0.216 |
| Choline | NP | NP | NP | NP | NP | NP |
| Total impurities | 1.21 | 1.20 | 1.25 | 0.40 | 0.41 | 0.42 |

TABLE 28

| | Composition 15 | | |
|---|---|---|---|
| Storage Condition | Initial | 25° C./ 60% RH | 2-8° C. |
| Duration | | 1 month | |
| Pack (MOC) | | Glass vial | Glass vial |
| Description | Clear, colorless solution free from visible particles | | |
| pH | 3.99 | 3.66 | 4.23 |

TABLE 28-continued

| | Composition 15 | | |
|---|---|---|---|
| Storage Condition | Initial | 25° C./ 60% RH | 2-8° C. |
| Assay (Succinylcholine chloride) | 101.4 | 101.2 | 101.9 |
| Osmolality (mOsmol/kg) | 312/ 1560 | 313 | 315 |
| | Impurities (% w/w) | | |
| Succinic acid | ND | 0.035 | 0.001 |
| Succinylmonocholine | 0.283 | 1.357 | 0.422 |
| Choline | NP | 0.77 | 0.24 |
| Total impurities | 0.4 | 1.39 | 0.42 |

TABLE 29

| | Composition 16 | | |
|---|---|---|---|
| Storage Condition | Initial | 25° C./ 60% RH | 2-8° C. |
| Duration | | 2W | 2W |
| Pack (MOC) | | Glass vial | Glass vial |
| Description | Clear, colorless solution free from visible particles | | |
| pH | 4.42 | 3.77 | 4.11 |
| Assay (Succinylcholine chloride) | 98.8 | 96.0 | 96.7 |
| Osmolality (mOsmol/kg) | 307/ 1535 | NP | NP |
| | Impurities (% w/w) | | |
| Succinic acid | ND | 0.012 | ND |
| Succinylmonocholine | 0.379 | 1.017 | 0.491 |
| Choline | NP | NP | NP |
| Total impurities | 0.58 | 1.51 | 0.90 |

TABLE 30

| | Composition 17 | | |
|---|---|---|---|
| Storage Condition | Initial | 25° C./60% RH | 2-8° C. |
| Duration | | 2W | 2W |
| Pack (MOC) | | Glass vial | Glass vial |
| Description | Clear, colorless solution free from visible particles | | |
| pH | 4.24 | 3.81 | 4.16 |
| Assay (Succinylcholine chloride) | 99.8 | 98.2 | 99.8 |

TABLE 30-continued

| | Composition 17 | | |
|---|---|---|---|
| Storage Condition | Initial | 25° C./60% RH | 2-8° C. |
| Osmolality (mOsmol/kg) | 307/1535 | NP | NP |
| Impurities (% w/w) | | | |
| Succinic acid | ND | 0.008 | ND |
| Succinylmonocholine | 0.335 | 1.055 | 0.459 |
| Choline | NP | NP | NP |
| Total impurities | 0.41 | 1.48 | 0.80 |

TABLE 31

| | Composition 18 | | |
|---|---|---|---|
| Storage Condition | Initial | 25° C./60% RH | 2-8° C. |
| Duration | | 2W | 2W |
| Pack (MOC) | | Glass vial | Glass vial |
| Description | | Clear, colorless solution free from visible particles | |
| pH | 4.29 | 4.06 | 4.22 |
| Assay (Succinylcholine chloride) | 99.0 | 96.8 | 98.2 |
| Osmolality (mOsmol/kg) | 308/1540 | NP | NP |
| Impurities (% w/w) | | | |
| Succinic acid | ND | 0.018 | ND |
| Succinylmonocholine | 0.616 | 1.366 | 0.756 |
| Choline | NP | NP | NP |
| Total impurities | 0.94 | 1.98 | 1.26 |

TABLE 32

| | Composition 19 | | |
|---|---|---|---|
| Storage Condition | Initial | 25° C./60% RH | 2-8° C. |
| Duration | | 2W | 2W |
| Pack (MOC) | | Glass vial | Glass vial |
| Description | | Clear, colorless solution free from visible particles | |
| pH | 4.28 | 4.15 | 4.21 |
| Assay (Succinylcholine chloride) | 99.7 | 97.2 | 97.7 |
| Osmolality (mOsmol/kg) | 319/1595 | NP | NP |
| Impurities (% w/w) | | | |
| Succinic acid | ND | 0.011 | ND |
| Succinylmonocholine | 0.321 | 1.21 | 0.446 |
| Choline | NP | NP | NP |
| Total impurities | 0.42 | 1.59 | 0.68 |

TABLE 33

| | Stability data for Composition A | | |
|---|---|---|---|
| Test | Initial | 25° C./40% RH 3M | 2-8° C. 6M |
| Pack | | PFS (COC) | PFS (COC) |
| Description | | Clear, colourless solution free from visible particles | |
| pH | 3.75 | 3.50 | 3.61 |
| Osmolality (mOsmol/kg) | 892* | 916* | 897* |
| Assay (Succinylcholine chloride) | 98.3 | 95.7 | 98.7 |

TABLE 33-continued

| | Stability data for Composition A | | |
|---|---|---|---|
| Test | Initial | 25° C./40% RH 3M | 2-8° C. 6M |
| Impurities (% w/w) | | | |
| Succinic Acid | ND | 0.13 | 0.007 |
| Succinylmonocholine | 0.09 | 2.09 | 0.624 |
| Limit of Choline | 0.03 | 1.54 | 0.31 |
| Total impurities | 0.27 | 4.41 | 1.11 |

*reported value is after 1:5 dilution with water.

TABLE 34

| | Stability data for Composition B | | |
|---|---|---|---|
| Test | Initial | 25° C./40% RH 3M | 2-8° C. 6M |
| Pack | | PFS (COC) | PFS (COC) |
| Description | | Clear, colourless solution free from visible particles | |
| pH | 3.72 | 3.36 | 3.56 |
| Osmolality (mOsmol/kg) | 706* | 750* | 770* |
| Assay (Succinylcholine chloride) | 97.8 | 95.3 | 98.3 |
| Impurities (% w/w) | | | |
| Succinic Acid | ND | 0.17 | 0.01 |
| Succinylmonocholine | 0.10 | 2.61 | 0.717 |
| Limit of Choline | 0.03 | 1.52 | 0.34 |
| Total impurities | 0.28 | 4.64 | 1.27 |

TABLE 35

| | Stability data for Composition C | | |
|---|---|---|---|
| Test | Initial | 25° C./40% RH 3M | 2-8° C. 9M |
| Pack | | PFS (COC) | PFS (COC) |
| Description | | Clear, colourless solution free from visible particles | |
| pH | 3.73 | 3.39 | NA |
| Osmolality (mOsmol/kg) | 590* | 599* | NA |
| Assay (Succinylcholine chloride) | 97.1 | 94.1 | NA |
| Impurities (% w/w) | | | |
| Succinic Acid | ND | 0.19 | 0.018 |
| Succinylmonocholine | 0.07 | 2.81 | 1.022 |
| Limit of Choline | 0.02 | 1.70 | 0.50 |
| Total impurities | 0.25 | 4.96 | 1.71 |

PFS: Prefilled syringe

TABLE 36

| | Stability data for Composition D | | |
|---|---|---|---|
| Test | Initial | 25° C./40% RH 3M | 2-8° C. 6M |
| Pack | | PFS (COC) | PFS (COC) |
| Description | | Clear, colourless solution free from visible particles | |
| pH | 3.65 | 3.35 | 3.60 |
| Osmolality (mOsmol/kg) | 444* | 3275 | 488* |
| Assay (Succinylcholine chloride) | 98.1 | 94.5 | 97.0 |

TABLE 36-continued

Stability data for Composition D

| Test | Initial | 25° C./40% RH 3M | 2-8° C. 6M |
|---|---|---|---|
| Impurities (% w/w) | | | |
| Succinic Acid | ND | 0.21 | 0.013 |
| Succinylmonocholine | 0.09 | 3.19 | 0.877 |
| Limit of Choline | 0.02 | 1.91 | 0.39 |
| Total impurities | 0.27 | 5.57 | 1.46 |

TABLE 37

Stability data for Composition F

| Test | Initial | 25° C./40% RH 2M | 2-8° C. 3M |
|---|---|---|---|
| Pack | | PFS (COC) | Glass Vial |
| Description | | Clear, colourless solution free from visible particles | |
| pH | 3.81 | 3.41 | 3.60 |
| Osmolality (mOsmol/kg) | 902 | 902 | 895 |
| Assay (Succinylcholine chloride) | 96.7 | 94.1 | 95.7 |
| Impurities (% w/w) | | | |
| Succinic Acid | ND | 0.11 | 0.01 |
| Succinylmonocholine | 0.195 | 2.43 | 0.59 |
| Limit of Choline | 0.07 | 1.33 | 0.26 |
| Total impurities | 0.27 | 4.06 | 0.97 |

TABLE 38

Stability data for Composition G

| Test | Initial | 25° C./40% RH 3M | 2-8° C. 6M |
|---|---|---|---|
| Pack | | PFS (COC) | PFS (COC) |
| Description | | Clear, colourless solution free from visible particles | |
| pH | 3.65 | 3.30 | 3.56 |
| Osmolality (mOsmol/kg) | 2103 | 2133 | 1954 |
| Assay (Succinylcholine chloride) | 96.7 | 92.0 | 98.7 |
| Impurities (% w/w) | | | |
| Succinic Acid | ND | 0.22 | 0.01 |
| Succinylmonocholine | 0.28 | 3.23 | 0.85 |
| Limit of Choline | 0.08 | 2.07 | 0.42 |
| Total impurities | 0.57 | 5.73 | 1.64 |

TABLE 39

Stability data for Composition H

| Test | Initial | 25° C./40% RH 3M | 2-8° C. 6M |
|---|---|---|---|
| Pack | | PFS (COC) | PFS (COC) |
| Description | | Clear, colourless solution free from visible particles | |
| pH | 3.73 | 3.35 | 3.53 |
| Osmolality (mOsmol/kg) | 964* | 929* | 944* |
| Assay (Succinylcholine chloride) | 98.7 | 95.2 | 98.6 |
| Impurities (% w/w) | | | |
| Succinic Acid | ND | 0.14 | 0.009 |
| Succinylmonocholine | 0.092 | 2.590 | 0.692 |

TABLE 39-continued

Stability data for Composition H

| Test | Initial | 25° C./40% RH 3M | 2-8° C. 6M |
|---|---|---|---|
| Limit of Choline | ND | 1.50 | 0.29 |
| Total impurities | 0.16 | 4.63 | 1.08 |

TABLE 40

Stability data for Composition I

| Test | Initial | 25° C./40% RH 3M | 2-8° C. 6M |
|---|---|---|---|
| Pack | | PFS (COC) | PFS (COC) |
| Description | | Clear, colourless solution free from visible particles | |
| pH | 3.63 | 3.28 | 3.56 |
| Osmolality (mOsmol/kg) | 276 | 286 | 284 |
| Assay (Succinylcholine chloride) | 97.9 | 90.5 | 98.6 |
| Impurities (% w/w) | | | |
| Succinic Acid | ND | 0.30 | 0.02 |
| Succinylmonocholine | 0.33 | 4.02 | 1.04 |
| Limit of Choline | 0.11 | 2.48 | 0.53 |
| Total impurities | 0.64 | 6.87 | 1.92 |

TABLE 41

Stability data for Composition J

| Test | Initial | 25° C./40% RH 1M | 2-8° C. 1M |
|---|---|---|---|
| Pack | | PFS (COC) | PFS (COC) |
| Description | | Clear, colourless solution free from visible particles | |
| pH | 3.55 | 3.42 | 3.57 |
| Osmolality (mOsmol/kg) | 485* | 495* | 494* |
| Assay (Succinylcholine chloride) | 99.8 | 97.3 | 99.3 |
| Impurities (% w/w) | | | |
| Succinic Acid | ND | 0.029 | 0.009 |
| Succinylmonocholine | 0.178 | 1.164 | 0.285 |
| Limit of Choline | 0.06 | 0.61 | 0.02 |
| Total impurities | 0.35 | 1.91 | 1.41 |

TABLE 42

Stability data for Composition K

| Test | Initial | 25° C./40% RH 2M | 2-8° C. 2M |
|---|---|---|---|
| Pack | | PFS (COC) | PFS (COC) |
| Description | | Clear, colourless solution free from visible particles | |
| pH | 3.69 | 3.37 | 3.59 |
| Osmolality (mOsmol/kg) | 536* | 537* | 542* |
| Assay (Succinylcholine chloride) | 99.1 | 95.9 | 97 |
| Impurities (% w/w) | | | |
| Succinic Acid | ND | 0.01 | 0.001 |
| Succinylmonocholine | 0.124 | 1.969 | 0.366 |
| Limit of Choline | 0.06 | 1.17 | 0.19 |
| Total impurities | 0.29 | 3.31 | 0.59 |

TABLE 43

Stability data for Composition L

| Test | Initial | 25° C./40% RH 1M | 2-8° C. 1M |
|---|---|---|---|
| Pack | | PFS (COC) | PFS (COC) |
| Description | | Clear, colourless solution free from visible particles | |
| pH | 3.69 | 3.51 | 3.59 |
| Osmolality (mOsmol/kg) | 1011* | 1022* | 1013* |
| Assay (Succinylcholine chloride) | 100.0 | 96.9 | 98.3 |
| Impurities (% w/w) | | | |
| Succinic Acid | ND | ND | ND |
| Succinylmonocholine | 0.103 | 0.891 | 0.13 |
| Limit of Choline | 0.09 | 0.48 | 0.15 |
| Total impurities | 0.30 | 1.44 | 0.39 |

TABLE 44

Stability data for Composition M

| Test | Initial | 25° C./40% RH 1M | 2-8° C. 1M |
|---|---|---|---|
| Pack | | PFS (COC) | PFS (COC) |
| Description | | Clear, colourless solution free from visible particles | |
| pH | 3.70 | 3.42 | 3.56 |
| Osmolality (mOsmol/kg) | 587* | 602* | 594* |
| Assay (Succinylcholine chloride) | 99.7 | 96.8 | 98.8 |
| Impurities (% w/w) | | | |
| Succinic Acid | ND | ND | ND |
| Succinylmonocholine | 0.143 | 1.121 | 0.372 |
| Limit of Choline | 0.14 | 0.51 | 0.13 |
| Total impurities | 0.37 | 1.68 | 0.52 |

Compositions A to M were found to be stable at 25° C./40% RH and 2-8° C. for at least 30 days. Compositions A-D, F-H & J (containing aliphatic polyols as stabilizing agents) were found to be physically and chemically stable for at least 30 days at 25° C./40% RH and 2-8° C. Composition K (containing ethanol as stabilizing agent) was also found to be physically and chemically stable for at least 30 days at 25° C./40% RH and 2-8° C.

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

The invention claimed is:

1. A pharmaceutical composition consisting of:
   (i) therapeutically effective amount of succinylcholine chloride at a concentration of from about 5 mg/mL to 60 mg/mL;
   (ii) propylene glycol as a stabilizing agent at a concentration of from about 20 mg/mL to about 300 mg/mL;
   (iii) water as a solvent;
   (iv) optionally one or more pH adjusting agents; and
   (v) optionally sodium chloride as a tonicity contributing agent at a concentration of from about 1 mg/mL to about 50 mg/mL
   wherein the composition is in the form of a ready to use aqueous solution suitable for parenteral administration, and wherein the aqueous solution has a pH of about 3 to about 5 and is stable at room temperature for at least 30 days.

2. The composition of claim 1, wherein succinylcholine chloride is present at a concentration of about 20 mg/mL.

3. The composition of claim 1, wherein the composition is free of tonicity contributing agent.

4. The composition of claim 1, wherein the composition is disposed in a pre-filled syringe or vial.

5. The composition of claim 1, wherein the composition has total impurities of less than about 6.0% (w/w) as measured by HPLC, when stored at 25° C./40% RH for up to 90 days.

6. The composition of claim 1, wherein the composition has succinic acid impurity of less than about 0.5% (w/w) as measured by HPLC, when stored at 25° C./40% RH for up to 90 days.

7. The composition of claim 1, wherein the composition has succinylmonocholine impurity of less than about 5.0% (w/w) as measured by HPLC, when stored at 25° C./40% RH for up to 90 days.

8. The composition of claim 1, wherein the composition has choline impurity of less than about 3.0% (w/w) as measured by HPLC, when stored at 25° C./40% RH for up to 90 days.

9. The pharmaceutical composition according to claim 4, wherein the pre-filled syringe is made up of a polymeric materials selected from the group consisting of polysulfone, polycarbonate, polypropylene, polyethylene, ethylene/propylene copolymers, polyolefins, acrylic-imide copolymers, polyester, poly (1,1,2,2 tetrafluoroethylene), Nylon, polyoxymethylene, polymethylpentene, polyvinylidene chloride, ethylvinylacetate, cyclic olefin polymer, cyclic olefin copolymer, crystal zenith, and mixtures thereof.

10. The pharmaceutical composition of claim 1, wherein the composition is sterilized using a technique selected from the group consisting of filtration through aseptic filtration-filling-sealing process, terminal sterilization, incorporation of sterilizing agents, irradiation, and heating.

11. A kit comprising the composition of claim 1, wherein the kit further comprises an injection device for administration of the composition to a subject in need of such pharmaceutical composition.

12. The kit of claim 11, wherein the injection device comprises a needle and prefilled syringe or syringe cartridge with the composition disposed therein.

13. A method of providing succinylcholine as an adjunct to general anaesthesia, to facilitate tracheal intubation, and to provide skeletal muscle relaxation during surgery or mechanical ventilation to a human subject in need thereof comprising administration of the subject the injectable pharmaceutical compositions of claim 1.

* * * * *